US008735173B2

(12) United States Patent
Meikle et al.

(10) Patent No.: US 8,735,173 B2
(45) Date of Patent: *May 27, 2014

(54) MULTIPLEX SCREENING FOR LYSOSOMAL STORAGE DISORDERS (LSDS)

(75) Inventors: Peter John Meikle, Redwood Park (AU); John Joseph Hopwood, Stonyfell (AU); Douglas Alexander Brooks, North Cheltenham (AU); Caroline Dean, Christies Beach (AU)

(73) Assignee: Women's and Children's Hospital, North Adelaide (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/432,387

(22) Filed: Mar. 28, 2012

(65) Prior Publication Data

US 2012/0184050 A1     Jul. 19, 2012

Related U.S. Application Data

(62) Division of application No. 10/551,396, filed as application No. PCT/AU2004/000403 on Mar. 31, 2004, now Pat. No. 8,173,443.

(30) Foreign Application Priority Data

| Mar. 31, 2003 | (AU) | ................................ 2003901451 |
| Aug. 8, 2003 | (AU) | ................................ 2003904174 |
| Sep. 1, 2003 | (AU) | ................................ 2003904720 |

(51) Int. Cl.
*G01N 33/543*     (2006.01)

(52) U.S. Cl.
CPC .................................... *G01N 33/543* (2013.01)
USPC ............ 436/518; 435/7.1; 435/7.92; 436/525

(58) Field of Classification Search
None
See application file for complete search history.

(56) References Cited

U.S. PATENT DOCUMENTS

| 5,501,957 | A | 3/1996 | Dennis et al. |
| 6,449,562 | B1 | 9/2002 | Chandler et al. |
| 6,524,793 | B1 | 2/2003 | Chandler et al. |
| 7,615,224 | B2 * | 11/2009 | Meikle et al. ............ 424/178.1 |
| 2003/0054356 | A1 | 3/2003 | Jacobson et al. |

FOREIGN PATENT DOCUMENTS

| WO | WO 97/44668 | 11/1997 |
| WO | WO 00/55632 | 9/2000 |
| WO | WO 03/106997 | 12/2003 |

OTHER PUBLICATIONS

O'Brien, et al.; Saposin Proteins: Structure, Function, and Role in Human Lysosomal Storage Disorders; The FASEB Journal, vol. 5, Mar. 1991, pp. 301-308.

Canadian Patent Office; Office Action; Canadian Patent Application No. 2,524,272, Aug. 29, 2011.
Written Argument as filed with the Japanese Patent Office on May 26, 2011, Japanese Serial No. 2006-503985.
Amendment as filed with the Japanese Patent Office on May 26, 2011, Japanese Serial No. 2006-503985.
Amendment as filed with the European Patent Office on Jun. 16, 2011, European Serial No. 04724491.8.
Japanese Patent Office, Reason of Rejection, Application No. 2006-503985, Dec. 7, 2010.
European Patent Office, Communication Pursuant to Article 94(3) EPC, Application No. 04 724 491.8, Feb. 25, 2011.
European Patent Office, Response to Official Action, Application No. 04724491.8, Jan. 24, 2011.
Note of Refutation as filed with Japanese Patent Office on Sep. 22, 2010, Japanese Application No. 2006-503,985.
(English Translation) Note of Refutation as filed with Japanese Patent Office on Sep. 22, 2010, Japanese Application No. 2006-503,985.
Amendment as filed with Japanese Patent Office on Sep. 22, 2010, Japanese Application No. 2006-503,985.
(English Translation) Amendment as filed with Japanese Patent Office on Sep. 22, 2010, Japanese Application No. 2006-503,985.
Japanese Patent Office, Notification of Reason for Rejection, Application No. 2006-503985, Apr. 6, 2010.
Suzuki, T., et al., A New Mass Screening Method of Fabry Disease, Journal of the Japanese Teratology Society, 2002, vol. 18, No. 2, p. 134 (68).
European Patent Office, Official Action, Feb. 12, 2010.
Chang M.H.Y. et al. Saposins A, B, C and D in Plasma of Patents with Lysosomal Storage Disorders. Clinical Chemistry 43: 8 1325 (2000).
Meikle, P.J., et al. Diagnosis of Lysosomal Storage Disorders: Evaluation of Lysosome-Associated Membrane Protein LAMP-I as a Diagnostic Marker. Clinical Chemistry 43: 8 1325-1335 (1997).
Meikle PJ, Ranieri E, Ravenscroft EM, Hua CT, Brooks DA, Hopwood JJ. Newborn screening for lysosomal storage disorders. Southeast Asian J Trop Med Public Health. 1999;30 Suppl 2:104-10.
Renlund, et al. Studies on the Defect Underlying the Lysosomal Storage of Sialic Acid in Salla Disease. The Journal of Clinical Investigation. 77(2):568-74 (Feb. 1986).
Umapathysivam, K., J.J. Hopwood, P.J. Meikle. Determination of acid alpha-glucosidase activity in blood spots as a diagnosis for Pompe Disease, Clin. Chem. 47(8): 1378-1383 (2001).
Umapathysivam, K., J.J. Hopwood, P.J. Meikle, Determination of acid alpha-glucosidase activity Protein: Evaluation as a Screening Marker for Pompe Disease and Other Lysosomal Storage Disorders, Clin. Chem. 46:9 1318-1325 (2000).
Whitfield PD, Nelson P, Sharp PC, Bindloss CA, Dean C, Ravenscroft M, Fong BA, Fietz MJ, Hopwood JJ, Meikle PJ. Correlation among genotype, phenotype, and biochemical markers in Gaucher disease: implications for the prediction of disease severity. Mol Genet Metab. Jan. 2002;75(1):46-55.

* cited by examiner

*Primary Examiner* — Gary W Counts
(74) *Attorney, Agent, or Firm* — Jackson Walker L.L.P.

(57) ABSTRACT

A novel protein profiling method of testing for Lysosomal Storage Diseases ("LSD") using discovered normalized lysosomal fingerprint patterns. The fingerprint patterns reveal the health of lysosomal organelles, specific LSD, and clinical severity. Multiplexing bead technology for simultaneous screening of multiple LSD and normalizing measured enzyme activity or protein levels against other lysosomal proteins, enzymes, or enzyme activities. Compounds, reagents, and methods for identifying and quantifying multiple target enzymes and proteins.

5 Claims, 34 Drawing Sheets

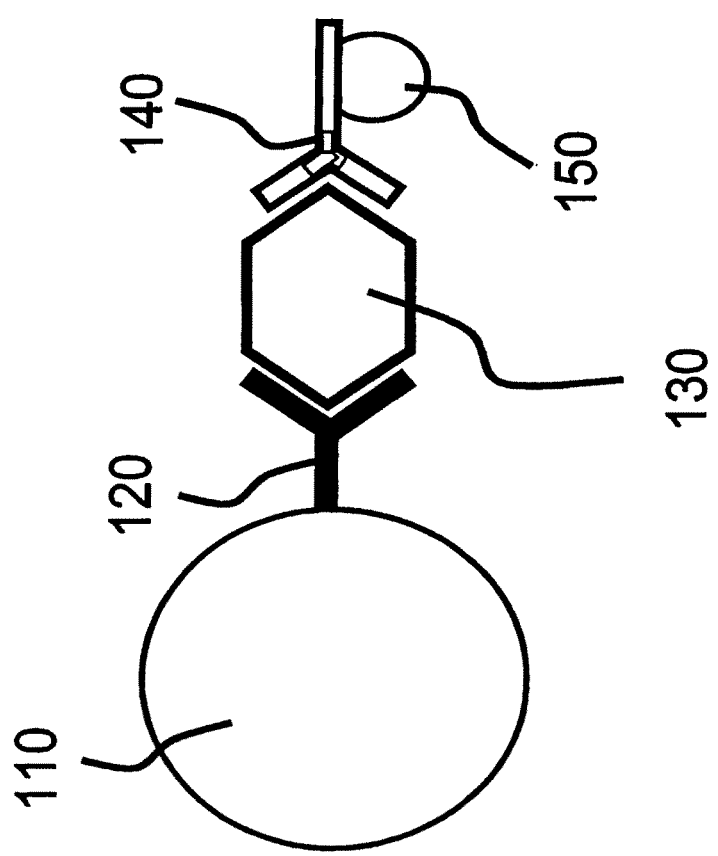

Antibody reagents available for lysosomal proteins

| Priority | Disorder | Enzyme /Protein Marker | Protein | Polyclonal | Monoclonal (Complementary) |
|---|---|---|---|---|---|
| 1 | | LAMP-1 | CHO ex | Sheep | 2 |
| 2 | | Saposin C | | Rabbit | 2 |
| 3 | | CD 45 | commercial | | |
| 4 | MPS I | α-L-iduronidase | CHO ex | Sheep | 1 |
| 5 | Pompe disease | α-glucosidase | CHO ex | Sheep | 1 |
| 6 | Gaucher disease | β-glucosidase | commercial | Sheep | 1 |
| 7 | Fabry disease | α-galactosidase A | commercial | Sheep | 2 |
| 8 | MPS VI | N-acetylgalactosamine 4-sulphatase | CHO ex | Sheep | 1 |
| 9 | Niemann-Pick A/B | acid sphingomyelinase | commercial | Sheep | 2 |
| 10 | MPS II | iduronate-2-sulphatase | CHO ex | Sheep | |
| 11 | MPS IVA | galactose 6-sulphatase | CHO ex | Rabbit | |
| 12 | MLD | arylsulphatase A | CHO ex | Sheep | |
| 13 | Krabbe disease | galactocerebrosidase | | | |
| 14 | MPS IIIA | heparan-N-sulphatase | CHO ex | Rabbit | 1 |
| 15 | MPS IIIB | α-N-acetylglucosaminidase | CHO ex | Rabbit | |

Figure 11

Protein markers for 7-Plex LSD screening

LAMP-1 and saposin C

| Disorder | Enzyme Deficiency | Australian Prevalence | Therapy |
| --- | --- | --- | --- |
| Gaucher disease | β-glucosidase | 1 in 57,000 | ERT / BMT |
| Fabry disease | α-galactosidase A | 1 in 117,000 | ERT |
| MPS I | α-L-iduronidase | 1 in 88,000 | ERT / BMT |
| Pompe disease | α-glucosidase | 1 in 146,000 | ERT (trials) |
| MPS VI | N-acetylgalactosamine 4-sulphatase | 1 in 235,000 | BMT / ERT (trials) |

- Most LSD patients have reduced protein.
- Total prevalence detected with 7-plex is 1 in 20,600.

Figure 20

Antibody reagents used in 7-plex assays

| Assay | Bead region | Capture antibody | µg/1.25e6 beads | Reporter antibody | ng/well |
|---|---|---|---|---|---|
| Lamp-1 | 25 | Sheep anti Lamp-1 polyclonal | 9 | Sheep anti Lamp-1 polyclonal | 16 |
| Saposin C | 42 | Monoclonal 7B2 | 9 | Monoclonal S13C1 G2 G3 | 8 |
| α-glucosidase | 26 | Sheep anti α-glucosidase polyclonal | 5 | Monoclonal 43D1 | 16 |
| α-iduronidase | 24 | Sheep anti α-iduronidase polyclonal | 36 | Monoclonal Id1A | 16 |
| α-galactosidase | 43 | Monoclonal AG2.GG9.6.1.6 | 9 | Monoclonal AG2.6F5.1151 | 32 |
| β-glucosidase | 45 | Sheep anti β-glucosidase polyclonal | 9 | Sheep anti β-glucosidase polyclonal | 32 |
| N-acetyl-galactosamine-4-sulphatase | 46 | Sheep anti 4-sulphatase polyclonal | 9 | Sheep anti 4-sulphatase polyclonal | 32 |

Figure 21

Adult control protein values in 7-plex assays

| Sample ID | Age years | LAMP-1 ng/mL | Saposin C ng/mL | α-iduronidase ng/mL | α-glucosidase ng/mL | β-glucosidase ng/mL | α-galactosidase ng/mL | N-acetyl galactosamine-4-sulphatase ng/mL |
|---|---|---|---|---|---|---|---|---|
| LDRU C7 EDTA | 39.1 | 32.9 | 12.7 | 5.0 | 7.7 | 3.3 | 4.6 | 0.9 |
| LDRU C9 EDTA | 44.1 | 36.4 | 10.7 | 4.8 | 4.0 | 3.0 | 4.2 | 1.5 |
| LDRU C11 EDTA | 43.2 | 34.5 | 8.9 | 7.5 | 8.2 | 3.5 | 4.6 | 1.2 |
| LDRU C12 EDTA | 47.2 | 28.7 | 13.2 | 10.0 | 8.8 | 4.1 | 7.4 | 1.7 |
| LDRU C13 EDTA | 25.2 | 36.5 | 14.0 | 6.3 | 9.2 | 3.0 | 5.9 | 0.9 |
| LDRU C14 EDTA | 22.8 | 38.5 | 22.3 | 7.9 | 14.0 | 6.4 | 8.5 | 2.3 |
| LDRU C15 EDTA | 32.3 | 38.8 | 13.5 | 11.2 | 10.8 | 5.3 | 4.6 | 1.5 |
| LDRU C16 EDTA | 23.9 | 31.0 | 12.0 | 4.9 | 9.4 | 3.5 | 2.7 | 1.3 |
| LDRU C17 EDTA | 24.8 | 34.7 | 13.0 | 8.2 | 5.6 | 4.4 | 4.2 | 1.1 |
| LDRU C18 EDTA | 26.3 | 29.1 | 12.1 | 4.3 | 5.3 | 4.0 | 5.1 | 1.1 |
| LDRU C19 EDTA | 39.8 | 36.2 | 13.0 | 5.9 | 6.9 | 3.7 | 3.6 | 1.7 |
| LDRU C20 EDTA | 31.8 | 40.9 | 17.6 | 8.5 | 10.1 | 5.5 | 7.2 | 1.8 |
| Average | 33.4 | 34.9 | 13.6 | 7.0 | 8.3 | 4.1 | 5.2 | 1.4 |
| StDev | 8.9 | 3.8 | 3.4 | 2.2 | 2.7 | 1.1 | 1.7 | 0.4 |
| Min | 22.8 | 28.7 | 8.9 | 4.3 | 4.0 | 3.0 | 2.7 | 0.9 |
| Max | 47.2 | 40.9 | 22.3 | 11.2 | 14.0 | 6.4 | 8.5 | 2.3 |
| StDev (MOM) | 0.3 | 0.1 | 0.3 | 0.3 | 0.3 | 0.3 | 0.3 | 0.3 |
| Min (MOM) | 0.7 | 0.8 | 0.7 | 0.6 | 0.5 | 0.7 | 0.5 | 0.6 |
| Max (MOM) | 1.4 | 1.2 | 1.6 | 1.6 | 1.7 | 1.5 | 1.6 | 1.6 |

Figure 23

Newborn control protein values

| Sample ID | Age years | LAMP-1 ng/mL | Saposin C ng/mL | α-iduronidase ng/mL | α-glucosidase ng/mL | β-glucosidase ng/mL | α-galactosidase ng/mL | N-acetyl galactosamine-4 sulphatase ng/mL |
|---|---|---|---|---|---|---|---|---|
| Newborn 1 |  | 23.3 | 4.1 | 1.4 | 1.1 | 1.5 | 1.0 | 0.2 |
| Newborn 2 |  | 24.9 | 3.9 | 1.8 | 1.4 | 1.3 | 1.3 | 0.2 |
| Newborn 3 |  | 65.1 | 36.7 | 4.0 | 3.7 | 2.7 | 6.5 | 2.2 |
| Newborn 4 |  | 72.1 | 58.2 | 1.7 | 12.1 | 5.2 | 13.5 | 2.2 |
| Newborn 5 |  | 54.2 | 56.4 | 2.1 | 12.5 | 4.5 | 9.6 | 2.8 |
| Newborn 6 |  | 69.0 | 36.6 | 0.9 | 10.2 | 4.1 | 17.8 | 2.0 |
| Newborn 7 |  | 44.7 | 30.3 | 1.8 | 6.6 | 3.7 | 6.4 | 3.5 |
| Newborn 8 |  | 19.1 | 3.7 | 1.4 | 1.0 | 0.8 | 1.0 | 0.2 |
| Newborn 9 |  | 42.5 | 19.8 | 3.3 | 3.8 | 3.1 | 5.5 | 1.6 |
| Newborn 10 |  | 52.6 | 43.9 | 4.1 | 9.4 | 3.9 | 6.6 | 2.4 |
| Newborn 11 |  | 20.9 | 3.9 | 1.8 | 1.1 | 1.1 | 0.9 | 0.2 |
| Newborn 12 |  | 36.8 | 34.1 | 1.4 | 6.6 | 2.9 | 5.8 | 2.7 |
| Newborn 13 |  | 56.2 | 64.4 | 2.9 | 13.6 | 5.6 | 15.9 | 3.8 |
| Newborn 14 |  | 70.5 | 55.7 | 2.8 | 12.9 | 5.0 | 14.4 | 2.7 |
| Newborn 15 |  | 81.1 | 45.6 | 1.6 | 8.3 | 4.1 | 18.5 | 1.9 |
| Newborn 16 |  | 63.9 | 54.8 | 3.0 | 12.8 | 5.7 | 12.6 | 2.5 |
| Newborn 17 |  | 83.7 | 72.2 | 2.6 | 13.3 | 6.4 | 29.0 | 3.3 |
| Newborn 18 |  | 64.8 | 58.4 | 3.9 | 9.4 | 5.7 | 14.3 | 4.8 |
| Newborn 19 |  | 82.4 | 67.8 | 3.4 | 9.6 | 6.6 | 71.0 | 3.3 |
| Newborn 20 |  | 69.1 | 61.6 | 5.7 | 21.0 | 6.5 | 14.6 | 3.7 |
| Newborn 21 |  | 47.2 | 24.2 | 3.6 | 9.1 | 3.1 | 8.0 | 1.5 |
| Newborn 22 |  | 63.2 | 83.9 | 5.6 | 16.7 | 6.4 | 16.6 | 4.8 |
| Newborn 23 |  | 60.2 | 43.3 | 2.9 | 7.1 | 4.6 | 11.1 | 3.0 |
| Newborn 24 |  | 70.7 | 31.7 | 2.7 | 11.9 | 4.2 | 22.4 | 2.1 |
| Newborn 25 |  | 62.7 | 35.8 | 3.5 | 10.0 | 3.6 | 10.9 | 2.5 |
| Newborn 26 |  | 82.4 | 64.5 | 3.4 | 10.1 | 5.4 | 25.9 | 3.3 |
| Newborn 27 |  | 60.7 | 32.1 | 3.2 | 9.6 | 4.1 | 12.7 | 1.9 |
| Newborn 28 |  | 86.5 | 74.4 | 2.2 | 18.8 | 16.4 | 72.2 | 4.7 |
| Average |  | 58.2 | 42.9 | 2.8 | 9.4 | 4.6 | 16.0 | 2.5 |
| StDev |  | 19.6 | 22.8 | 1.2 | 5.1 | 2.9 | 17.3 | 1.3 |
| Min |  | 19.1 | 3.7 | 0.9 | 1.0 | 0.8 | 0.9 | 0.2 |
| Max |  | 86.5 | 83.9 | 5.7 | 21.0 | 16.4 | 72.2 | 4.8 |
| StDev (MOM) |  | 0.3 | 0.5 | 0.4 | 0.5 | 0.6 | 1.1 | 0.5 |
| Min (MOM) |  | 0.3 | 0.1 | 0.3 | 0.1 | 0.2 | 0.1 | 0.1 |
| Max (MOM) |  | 1.5 | 2.0 | 2.0 | 2.2 | 3.6 | 4.5 | 1.9 |

Figure 24

Pearson correlation coefficients for protein markers in dried blood spots from newborns.

| | LAMP-1 | Saposin C | α-Iduronidase | α-glucosidase | β-glucosidase | α-galactosidase | N-acetylgalactosamine-4-sulphatase |
|---|---|---|---|---|---|---|---|
| LAMP-1 | 1.00 | 0.82[a] | 0.31 | 0.73[a] | 0.70[a] | 0.69[a] | 0.68[a] |
| Saposin C | 0.82[a] | 1.00 | 0.47 | 0.85[a] | 0.75[a] | 0.61[a] | 0.88[a] |
| α-Iduronidase | 0.31 | 0.47[b] | 1.00 | 0.48[a] | 0.22 | 0.09 | 0.51[a] |
| α-glucosidase | 0.73[a] | 0.85[a] | 0.48[a] | 1.00 | 0.77[a] | 0.51[a] | 0.77[a] |
| β-glucosidase | 0.70[a] | 0.75[a] | 0.22 | 0.77[a] | 1.00 | 0.81[a] | 0.74[a] |
| α-galactosidase | 0.69[a] | 0.61[a] | 0.09 | 0.51[a] | 0.81[a] | 1.00 | 0.52[a] |
| N-acetylgalactosamine-4-sulphatase | 0.68[a] | 0.88[a] | 0.51[a] | 0.77[a] | 0.74[a] | 0.52[a] | 1.00 |

|  | Age | LAMP-1 | Saposin C | α-iduronidase | α-glucosidase | β-glucosidase | α-galactosidase | N-acetyl galactosamine-4-sulphatase |
|---|---|---|---|---|---|---|---|---|
|  |  | ng/mL | ng/mL | ng/mL | ng/mL | ng/mL | ng/mL | ng/mL |
| Adult Control[a] |  |  |  |  |  |  |  |  |
| Average | 33.4 | 34.9 | 13.6 | 7.0 | 8.3 | 4.1 | 5.2 | 1.4 |
| StDev | 8.9 | 3.8 | 3.4 | 2.2 | 2.7 | 1.1 | 1.7 | 0.4 |
| Min | 22.8 | 28.7 | 8.9 | 4.3 | 4.0 | 3.0 | 2.7 | 0.9 |
| Max | 47.2 | 40.9 | 22.3 | 11.2 | 14.0 | 6.4 | 8.5 | 2.3 |
| Patient[b] |  |  |  |  |  |  |  |  |
| Fabry | 38.15 | 35.55 | 29.24[c] | 2.85[d] | 6.32 | 4.19 | 0.00[d] | 1.95 |
| Fabry | 34.86 | 37.48 | 27.34[c] | 7.76 | 9.94 | 4.30 | 0.00[d] | 1.32 |
| Fabry | 26.95 | 29.56 | 8.60[d] | 4.03[d] | 5.92 | 2.76[d] | 0.00[d] | 0.57[d] |
| MPS I | NA | 30.01 | 7.71[d] | 0.27[d] | 4.96 | 1.21[d] | 1.87[d] | 0.53[d] |
| MPS I | 0.77 | 35.74 | 11.11 | 0.00[d] | 6.51 | 2.36[d] | 5.97 | 1.14 |
| MPS II | 3.89 | 52.15[c] | 37.13[c] | 8.90 | 8.21 | 4.04 | 6.99 | 2.28[c] |
| MPS VI | 4.84 | 40.74 | 11.76 | 6.41 | 7.24 | 3.45 | 3.98 | 0.00[d] |
| MPS VI | NA | 29.03 | 11.66 | 5.35 | 4.25 | 1.58[d] | 3.43 | 0.00[d] |
| ML II/II | 0.94 | 44.07[c] | 31.60[c] | 59.02[c] | 27.76[c] | 4.99 | 3.48 | 5.10[c] |
| ML II/II | 1.92 | 44.69[c] | 74.10[c] | 33.66[c] | 36.38[c] | 8.71[c] | 6.74 | 9.91[c] |
| Pompe | 39.21 | 44.83[c] | 16.56 | 8.49 | 0.13[d] | 5.55 | 8.48 | 1.98 |
| Pompe | 24.40 | 35.89 | 12.73 | 6.54 | 0.19[d] | 2.80[d] | 3.68 | 2.10 |
| Pompe | 24.40 | 36.61 | 16.99 | 3.77[d] | 0.15[d] | 2.43[d] | 3.78 | 1.47 |
| Pompe | 57.80 | 35.30 | 20.62 | 5.42 | 0.00[d] | 3.89 | 4.03 | 1.41 |
| Pompe | 10.65 | 34.75 | 10.91 | 2.44[d] | 0.00[d] | 2.65[d] | 12.51[c] | 1.28 |
| Pompe | 8.35 | 34.51 | 15.93 | 4.43 | 0.07[d] | 3.95 | 2.12[d] | 1.06 |
| Pompe | 10.56 | 44.09[c] | 27.31[c] | 7.21 | 0.09[d] | 4.46 | 8.74[c] | 1.67 |

[a] Adult controls (n=12); [b] MPS = mucopolysaccharidosis; ML = mucolipidosis.
[c] indicates above control range; [d] indicates below control range

Figure 26

| | Age | LAMP-1 | Saposin C | α-Iduronidase | α-glucosidase | β-glucosidase | α-galactosidase | N-acetyl-galactosamine-4-sulphatase |
|---|---|---|---|---|---|---|---|---|
| | | ng/mL | ng/mL | ng/mL | ng/mL | ng/mL | ng/mL | ng/mL |
| Newborn Controls[a] | | | | | | | | |
| Average | | 58.2 | 42.9 | 2.8 | 9.4 | 4.6 | 16.0 | 2.5 |
| StDev | | 19.6 | 22.8 | 1.2 | 5.1 | 2.9 | 17.3 | 1.3 |
| Min | | 19.1 | 3.7 | 0.9 | 1.0 | 0.8 | 0.9 | 0.2 |
| Max | | 86.5 | 83.9 | 5.7 | 21.0 | 16.4 | 72.2 | 4.8 |
| Patient[b] | | | | | | | | |
| Fabry | 38.15 | 35.55 | 29.24 | 2.85 | 6.32 | 4.19 | 0.00[d] | 1.95 |
| Fabry | 34.86 | 37.48 | 27.34 | 7.76[c] | 9.94 | 4.30 | 0.00[d] | 1.32 |
| Fabry | 26.95 | 29.56 | 8.60 | 4.03 | 5.92 | 2.76 | 0.00[d] | 0.57 |
| MPS I | NA | 30.01 | 7.71 | 0.27[d] | 4.96 | 1.21 | 1.87 | 0.53 |
| MPS I | 0.77 | 35.74 | 11.11 | 0.00[d] | 6.51 | 2.36 | 5.97 | 1.14 |
| MPS VI | 4.84 | 40.74 | 11.76 | 6.41[c] | 7.24 | 3.45 | 3.98 | 0.00[d] |
| MPS VI | NA | 29.03 | 11.66 | 5.35 | 4.25 | 1.58 | 3.43 | 0.00[d] |
| ML II/III | 0.94 | 44.07 | 31.60 | 59.02[c] | 27.76[c] | 4.99 | 3.48 | 5.10[c] |
| ML II/III | 1.92 | 44.69 | 74.10 | 33.66[c] | 36.38[c] | 8.71 | 6.74 | 9.91[c] |
| Pompe | | 44.83 | 16.56 | 8.49[c] | 0.13[d] | 5.55 | 8.48 | 1.98 |
| Pompe | 39.21 | 35.89 | 12.73 | 6.54[c] | 0.19[d] | 2.80 | 3.68 | 2.10 |
| Pompe | 24.40 | 36.61 | 16.99 | 3.77 | 0.15[d] | 2.43 | 3.78 | 1.47 |
| Pompe | 57.80 | 35.30 | 20.62 | 5.42 | 0.00[d] | 3.89 | 4.03 | 1.41 |
| Pompe | 10.65 | 34.75 | 10.91 | 2.44 | 0.00[d] | 2.65 | 12.51 | 1.28 |
| Pompe | 8.35 | 34.51 | 15.93 | 4.43 | 0.07[d] | 3.95 | 2.12 | 1.06 |
| Pompe | 10.56 | 44.09 | 27.31 | 7.21[c] | 0.09[d] | 4.46 | 8.74 | 1.67 |

[a] Newborn controls (n=28); [b] MPS = mucopolysaccharidosis; ML = mucolipidosis.
[c] indicates above control range; [d] indicates below control range

Figure 27

Summary of retrospective analysis of newborn blood spots

| Disorder | n | Markers | Sensitivity/ Specificity |
|---|---|---|---|
| α-Mannosidosis | 1 | H2/HNAc | 100 / 99.6 |
| MPS II | 4 | - | - |
| MPS IIIA | 2 | HNAc-UA-HNAc-UA | 100 / 100 |
| MPS IVA | 3 | HNAcS | 100 / 100 |
| I-cell disease | 2 | GC/LC | 100 / 100 |
| Sialidosis | 3 | HNS-UA | 67 / 100 |
| Pompe disease | 3 | - | - |
| Sandhoff disease | 6 | - | - |
| Tay-Sachs disease | 2 | HNAc-UA | 100 / 99.6 |

Figure 33

Protein markers for LSD screening

| Disorder | Enzyme Deficiency | Australian Prevalence | Therapy |
|---|---|---|---|
| Gaucher disease | β-glucosidase | 1 in 57,000 | ERT |
| Fabry disease | α-galactosidase A | 1 in 117,000 | ERT |
| MPS I | α-L-iduronidase | 1 in 88,000 | ERT |
| Pompe disease | α-glucosidase | 1 in 146,000 | ERT (trials) |
| MPS VI | N-acetylgalactosamine 4-sulphatase | 1 in 235,000 | ERT (trials) |
| MPS II | iduronate-2-sulphatase | 1 in 136,000 | ERT (trials) |
| Krabbe disease | galactocerebrosidase | 1 in 201,000 | BMT |
| MLD | arylsulphatase A | 1 in 92,000 | BMT |
| MPS IVA | galactose 6-sulphatase | 1 in 169,000 | ERT (proposed) |
| Niemann-Pick type A/B | acid sphingomyelinase | 1 in 248,000 | ERT (proposed) |
| MPS IIIA | heparan-N-sulphatase | 1 in 114,000 | Research |
| MPS IIIB | α-N-acetylglucosaminidase | 1 in 211,000 | Research |
| TOTAL (n = 12) | | 1 in 10,500 | |

Figure 34

MULTIPLEX SCREENING FOR LYSOSOMAL STORAGE DISORDERS (LSDS)

RELATED APPLICATIONS

This application is a divisional application of, and claims priority to, U.S. patent application Ser. No. 10/551,396, now U.S. Pat. No. 8,173,443, entitled "Multiplex Screening for Lysosomal Storage Disorders," filed on Oct. 19, 2006, which is a 371 application based on PCT Application No. PCT/AU04/00403 filed Mar. 31, 2004, which claims priority to the following applications: (1) Australian Provisional Patent Application Serial Number 2003/901451, entitled "AN IMPROVED METHOD OF SCREENING FOR LYSOSOMAL STORAGE DISORDERS," filed on Mar. 31, 2003, having Hopwood et al., listed as inventors; (2) Australian Provisional Patent Application, Serial Number 2003/904174, entitled "MULTIPLEX SCREENING FOR LSD'S," filed on Aug. 8, 2003, having Hopwood et al., listed as inventors; (3) Australian Provisional Patent Application, Serial Number 2003/904720, entitled "MULTIPLEX SCREENING FOR LSD'S," filed on Sep. 2, 2003, having Hopwood et al., listed as inventors. The entire content of each of the above identified applications is hereby incorporated by reference.

BACKGROUND

The present invention is generally related to diagnostics that determine Lysosomal Storage Disorders ("LSDs") and related diseases in a subject. More particularly, this invention pertains to compounds, reagents, and methods for identifying and quantifying the levels and ratios of multiple target antigens that are used to accurately diagnose LSD. The target antigens are naturally present in biological fluids or tissues of either LSD or non-LSD patients.

LSDs represent a group of over 40 distinct genetic diseases that generally affect young children. Individuals that are affected with a TSD present a wide range of clinical symptoms that depend upon the specific disorder or a particular genotype involved. The clinical symptoms associated with LSD's can have a devastating impact on both the child and the family of affected individuals. For example, central nervous system dysfunction, behavioral problems, and severe mental retardation are characteristic of many LSDs. Other clinical symptoms may include skeletal abnormalities, organomegaly, corneal clouding and dysmorphic features (Neufeld and Muenzer, 1995). Patients are usually born without the visible features of a LSD, but early stage symptoms can quickly develop into a progressive clinical concern. In severe cases, the affected children require constant medical management but still often die before adolescence.

The significance of LSDs to health care becomes obvious when comparing the group incidence rate for a LSD (1:5,000 births) to the group incidence rate of other with well-known and intensively studied genetic disorders, such as phenylketonuria (1:14,000) and cystic fibrosis (1:2,500), wherein these figures reflect incidence rates for Caucasian populations.

Once an individual begins to present the symptoms of a LSD, the actual clinical diagnosis of the disease is still a complex process. A clinical diagnosis of a LSD often requires multiple visits to a range of specialists, which can take months or even years. This long process is extremely stressful on the patient and family. Fortunately, there has been considerable progress in the diagnosis of LSDs over the past 20 years. For example, the development and introduction of chromatographic-based urine screens for a specific group of LSDs called mucopolysaccharidoses ("MPS") and oligosaccharidoses has facilitated screening of clinically selected patients for these disorders. Following a clinical index of suspicion for the disorders, the next stage of diagnosis involves a urine screen, wherein a "positive" urine screen is then followed by specific enzymatic analysis. Although the chromatographic-based screening methods are simple to perform, they are relatively labor-intensive and often require experience to accurately interpret results. One example includes a method of identifying and quantitating biochemical markers ("biomarkers") that are present in biological fluids or tissues of a patient having a MPS or related disorders comprises determining a target quantity of a target MPS biomarker oligosaccharide from a target biological sample taken from the target animal, and then comparing the target quantity to a reference quantity of a reference MPS biomarker oligosaccharide for the diagnosis, characterization, monitoring, and clinical management of MPS and related disease, as described in PCT Application AU03/00731 entitled "identification of Oligosaccharides and their Use in the Diagnosis and Evaluation of Mucopolysaccharidoses and Other Related Disorders," filed on Jun. 13, 2003 with Hopwood et al., listed as inventors (the entire content of PCT Application AU03/00731 is hereby incorporated by reference). Consequently, chromatographic-based screening tests for LSDs are not used in some centers. Furthermore, these chromatographic-based screens are not readily amenable to automation, which has further limited their utilization in screening strategies for newborns.

The production of specific substrates and antibody capture assays has made the enzymatic analyses for LSDs more accurate. Although not wanting to be bound by theory, the majority of LSDs result from a reduction in levels of a particular enzyme(s) involved in a specific LSD, and the identification of the specific enzyme(s) steady state in normal individuals will help identify the particular form of LSD in the affected individual. The ability to quickly and accurately determine the levels of the more than 40 enzymes known to be involved with LSDs will assist in the development of better and more economical screening assays. Unfortunately, many of the chromatographic-based screens and enzyme assays mentioned above are time-consuming, invasive, complex, and require cultured cells, or tissue biopsies, which tends to make such assays inconvenient and expensive. As a result, testing for a LSD is often not a first line strategy for an affected child with early stage symptoms. Newborn screening for LSDs promises to provide early detection of the LSD, but all newborns must be screened in order to detect the disease early. Patients having a family history of LSDs may have a justifiable reason to perform an early screen for a LSD. However, the cost of an early screen of the LSD in individuals not having a family history may not be justified economically. Therefore, it would be beneficial that any LSD screening process be capable of economically screening large numbers of newborns.

One common feature of LSDs is the accumulation and storage of materials within lysosomes. It is generally recognized that the accumulation and storage of material in LSD affected individuals results in an increase in the number and the size of lysosomes within a cell from approximately 1% to as much as 50% of total cellular volume. In non-affected individuals, such materials are typically degraded into degradation products within the lysosome and then transported across the lysosomal membrane. Certain lysosomal proteins are present at elevated levels in the lysosomes of affected individuals (Meikle et al., 1997; Hua et al., 1998). These identified proteins are useful biomarkers for an early diagnosis of all LSDs. For example, sensitive immunoquantification assays have been developed to monitor the level of useful biomarkers such as the lysosome-associated membrane proteins ("LAMPs"), saposins, and α-glucosidase. Although the determination of either LAMP-1 or LAMP-2 levels alone in an 'at-increased-risk' group will identify up to 65% of LSD affected individuals, the combination of a LAMP with one of the saposins increase identification of LSD affected individuals to approximately 85%. Therefore, a method to identify two or more biomarkers simultaneously would increase the accuracy of diagnosing a specific LSD as compared to any single assay. An automated multiplex assay that could perform a simultaneous screen on each of the known LSD deficient enzymes would reduce time and cost for accurate LSD diagnosis.

Multiplexing Bead Technology is built around 3 core technologies. The first is the family of fluorescently dyed microspheres having specific biomolecules bound to the surface of the microsphere. The second is a flow cytometer with 2 lasers and associated optics to measure biochemical reactions that occur on the surface of the microspheres, and the third is a high-speed digital signal processor to efficiently manage the fluorescent output. This type of system has been described in, for example: U.S. Pat. Nos. 6,449,562; 6,524,793 and U.S. patent application Ser. No. 09/956,857. U.S. Pat. No. 6,449,562 ("the '562 patent") entitled "Multiplexed Analysis of Clinical Specimens Apparatus, and Method," having Chandler et al. listed as inventors was issued on Sep. 10, 2002. The '562 patent discloses a method for the multiplexed diagnostic and genetic analysis of enzymes, DNA fragments, antibodies, and other biomolecules comprising the steps of constructing an appropriately labeled headset, exposing the headset to a clinical sample, and analyzing the combined sample/beadset by flow cytometry. Flow cytometric measurements are used to classify, in real-time, beads within an exposed headset and textual explanations, based on the accumulated data obtained during real-time analysis, are generated for the user. The inventive technology of the '562 patent enables the simultaneous, and automated, detection and interpretation of multiple biomolecules or DNA sequences in real-time while also reducing the cost of performing diagnostic and genetic assays. However, the '562 patent does not describe how to utilize the technology for diagnosing LSD's.

U.S. Pat. No. 6,524,793 ("the '793 patent") entitled "Multiplexed Analysis of Clinical Specimens Apparatus and Method," having Chandler et al. listed as inventors, was issued on Feb. 25, 2003. The '793 patent discloses a method for the multiplexed diagnostic and genetic analysis of enzymes, DNA fragments, antibodies, and other biomolecules comprising the steps of constructing an appropriately labeled beadset, exposing the headset to a clinical sample, and analyzing the combined sample/beadset by flow cytometry. Flow cytometric measurements are used to classify, in real-time, beads within an exposed beadset and textual explanations, based on the accumulated data obtained during real-time analysis, are generated for the user. The '793 patent enables the simultaneous, and automated, detection and interpretation of multiple biomolecules or DNA sequences in real-time while also reducing the cost of performing diagnostic and genetic assays. However, the '793 patent does not describe how to utilize the technology for diagnosing LSD's.

U.S. patent application Ser. No. 09/956,857 ("the '857 Application") entitled "Multiple Reporter Read-out for Bioassays" was published on Mar. 20, 2003. The '857 Application describes a method for detecting a plurality of reactive sites on an analyte, comprising allowing reactants on an addressable microsphere and the reactive sites to react, forming reactant-reactive site pairs distinguishable by fluorescence intensity. The '857 Application also provides a method for detecting a plurality of analytes in a sample using addressable microspheres in combination with one or more reporter reagents. Also provided are a method for determining allele zygosity of a genetic locus having two alleles or more alleles using microparticles, and a method for detecting a plurality of SNPs in nucleic acid molecules. The '857 Application also provides a composition comprising an addressable microsphere carrying at least two fluorescent reactants capable of forming reactant-analyte pairs distinguishable by their fluorescence intensity, and kits comprising the inventive composition and a plurality of reporter reagents. However, the '857 Application does not describe how to utilize the technology for diagnosing LSD's. The entirety of each of the applications or patents listed above is hereby specifically incorporated by reference.

Accordingly, there is a need for the development of a fast, accurate and economical screen for early diagnosis of LSDs, which is amenable to automation. The ability to identify specific LSD enzymes in an automated multiplex assay will have a significant impact on the development of a newborn screening programs, as well as the ability to address a number of other issues associated with the early diagnosis and treatment of LSDs. The present invention provides compounds, reagents, and methods for a LSD diagnostic multiplex assay.

FIGURES

FIG. 1 shows LAMP-1 levels in plasma from LSD individuals wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 2 shows saposin C levels in plasma from LSD individuals wherein the box length is the interquartile range that covers 25th to 75th percentile, the outliers are represented by (circles) each of these cases represent values between 1.5 and 3 box lengths from the upper or lower edge of the box; and the extreme outlier (stars) are cases with values more than 3 box lengths from the upper or lower edge of the box;

FIG. 3 shows α-Glucosidase in plasma from LSD affected individuals, wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 4 shows analysis of patient blood spots for LAMP-1 wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 5 shows Analysis of patient blood spots for saposin C wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 6 shows α-Glucosidase protein/activity determination in dried blood spots, wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 10 shows a microsphere capture sandwich immunoassay having a microsphere with two spectrally distinct fluorophores, the target LSD capture antibody and the unique LSD target protein or target antigen bound to the target LSD capture antibody and a reporter molecule;

FIG. 11 shows a list of antibody reagents available for lysosomal proteins for utilization of LSD's screened by multiplex technology;

Figure 17:
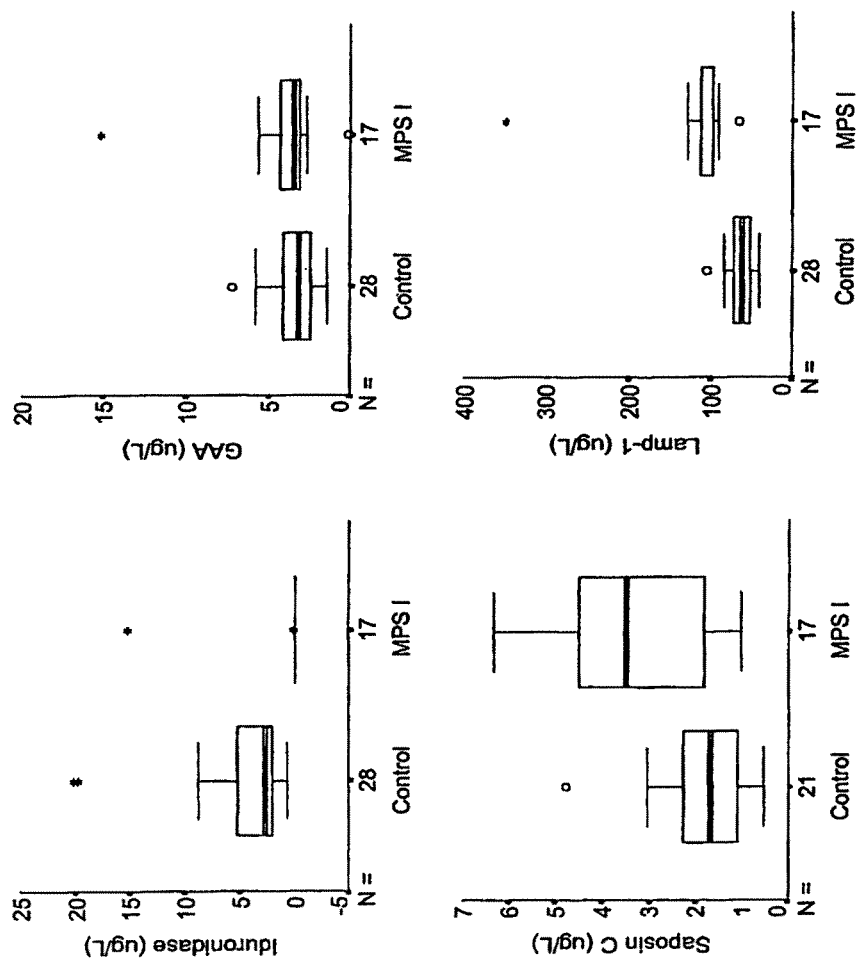
Figure 18:
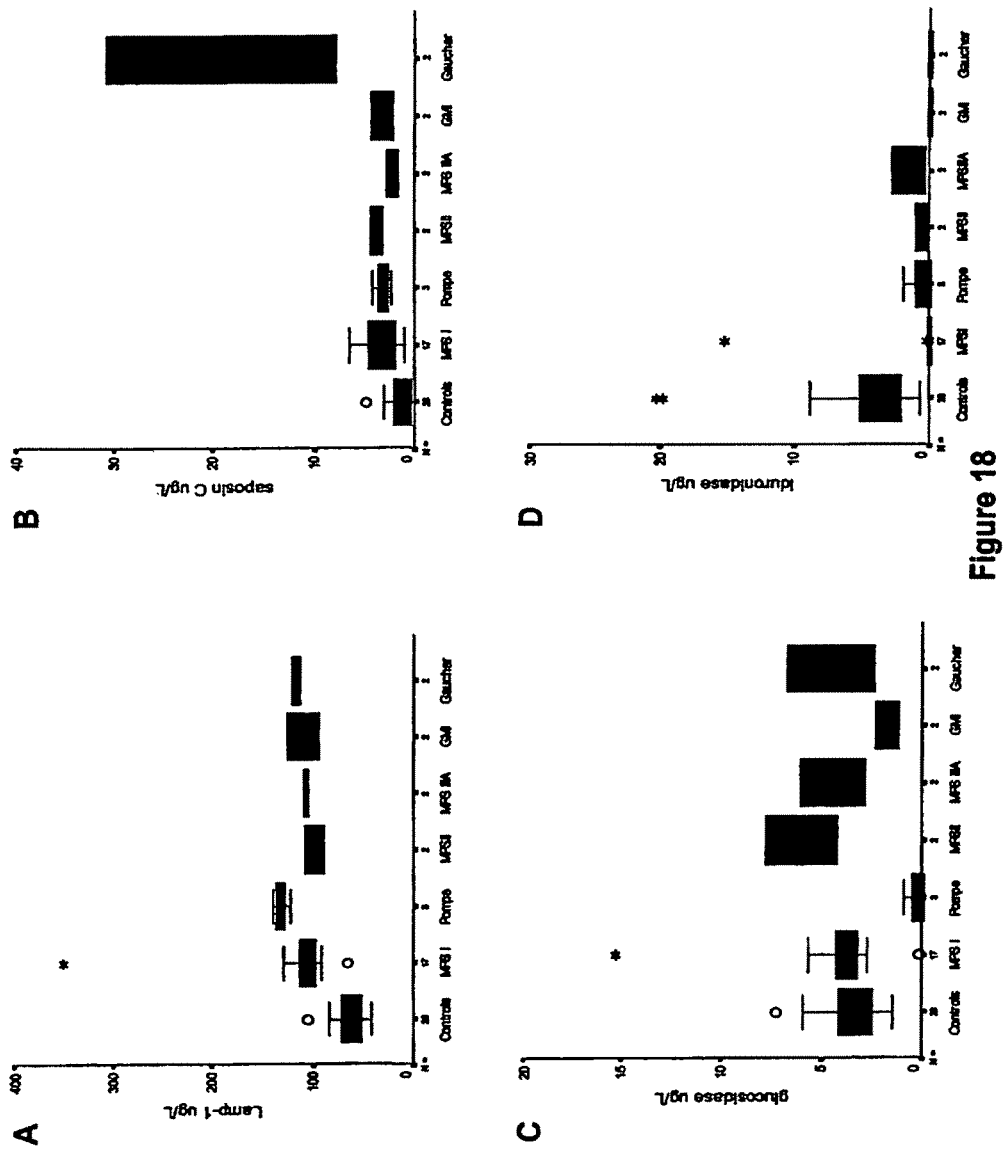

FIG. 17 shows multiplex analysis of control and MPS I plasma, wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 18 shows box plots of plasma concentrations of Lamp-1 (A), saposin C (B), α-glucosidase (C) and α-iduronidase (D) from a control group and 6 different LSD wherein, the center line within the box represents the median, the top of the box is the $75^{th}$ and the bottom of the box is the $25^{th}$ percentile, error bars represent the largest and smallest values that are not outliers, outliers represented by open circles, are values more than 1.5 box lengths from the $75^{th}$ and $25^{th}$ percentile and extremes represented by stars are values more than 3 box-lengths from the $75^{th}$ and $25^{th}$ percentile.

Figure 19:
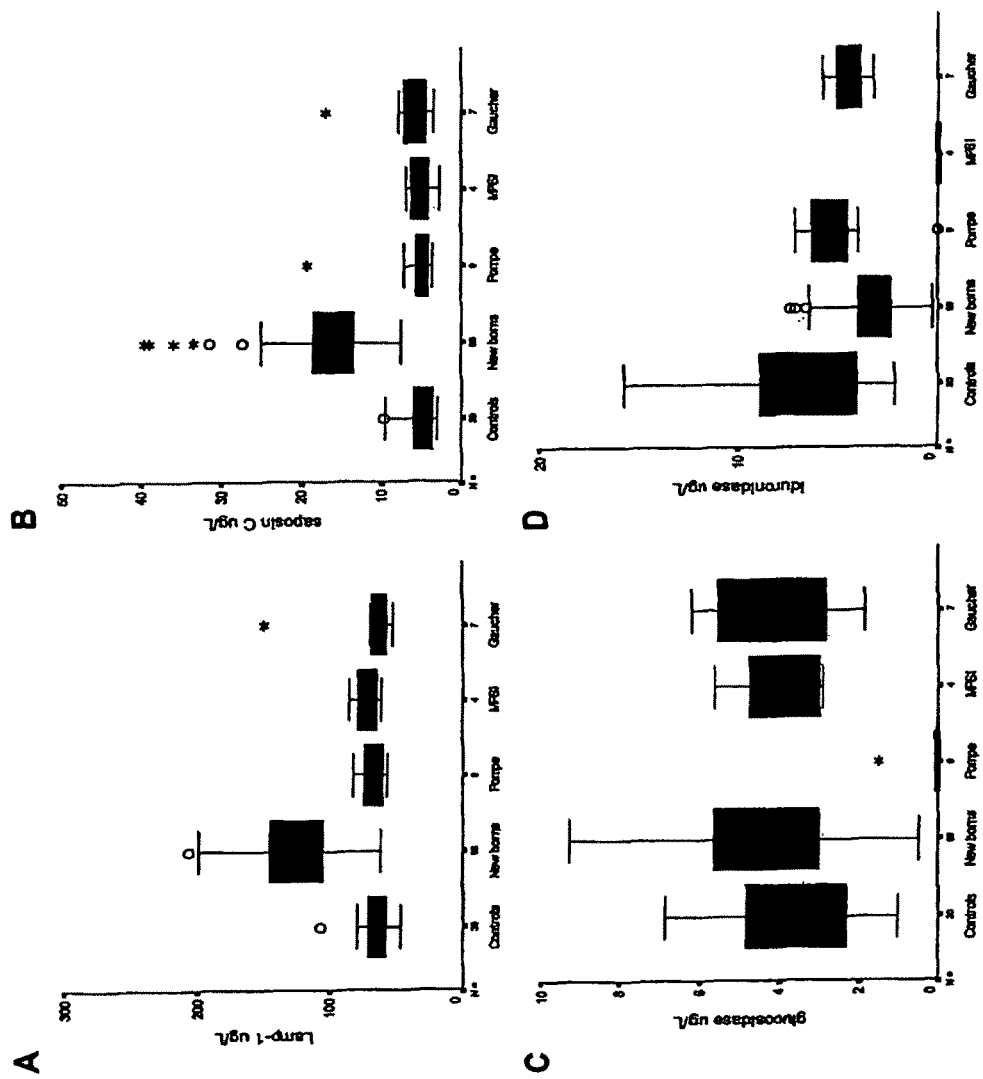

FIG. 19 shows box plots of concentrations of Lamp-1 (A), saposin C (B), α-glucosidase (C) and α-iduronidase (D) from dried blood spots, the samples were measured in a control group, a newborn group, and a group of 3 LSD patients.

Figure 22:
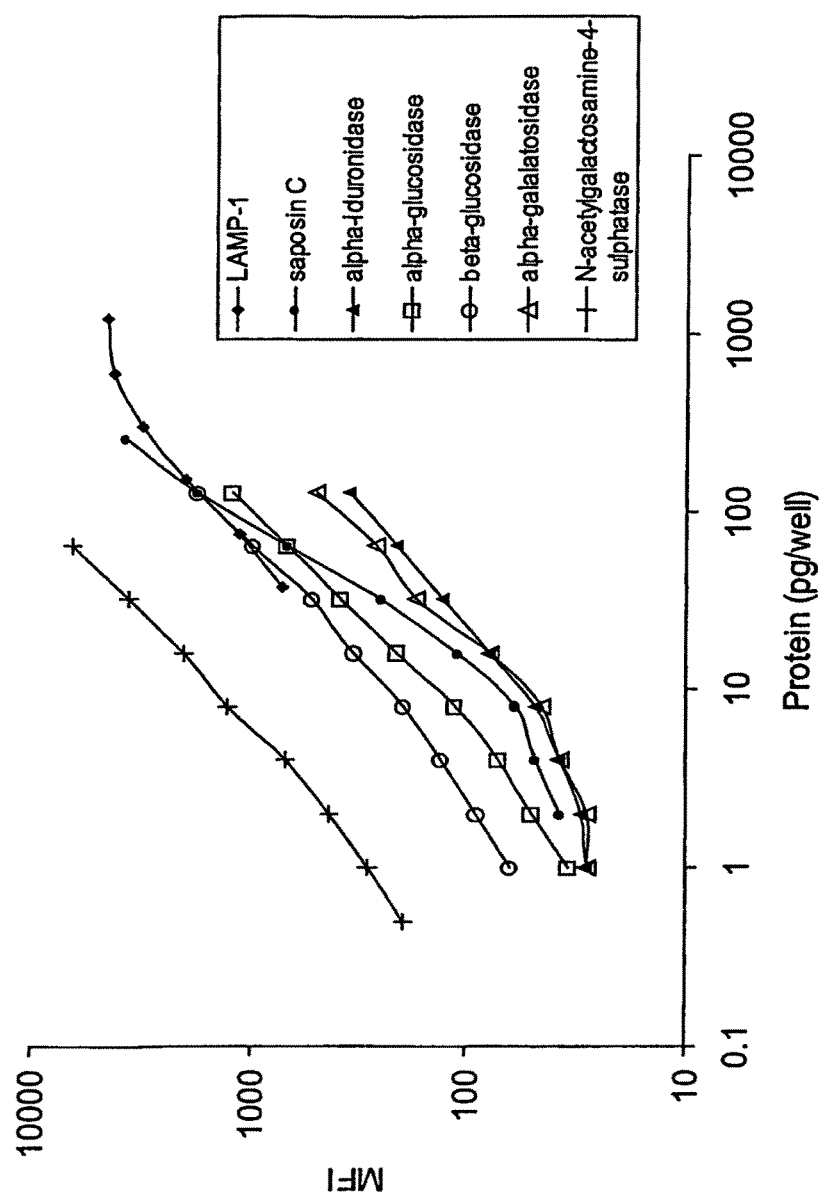
Figure 28:
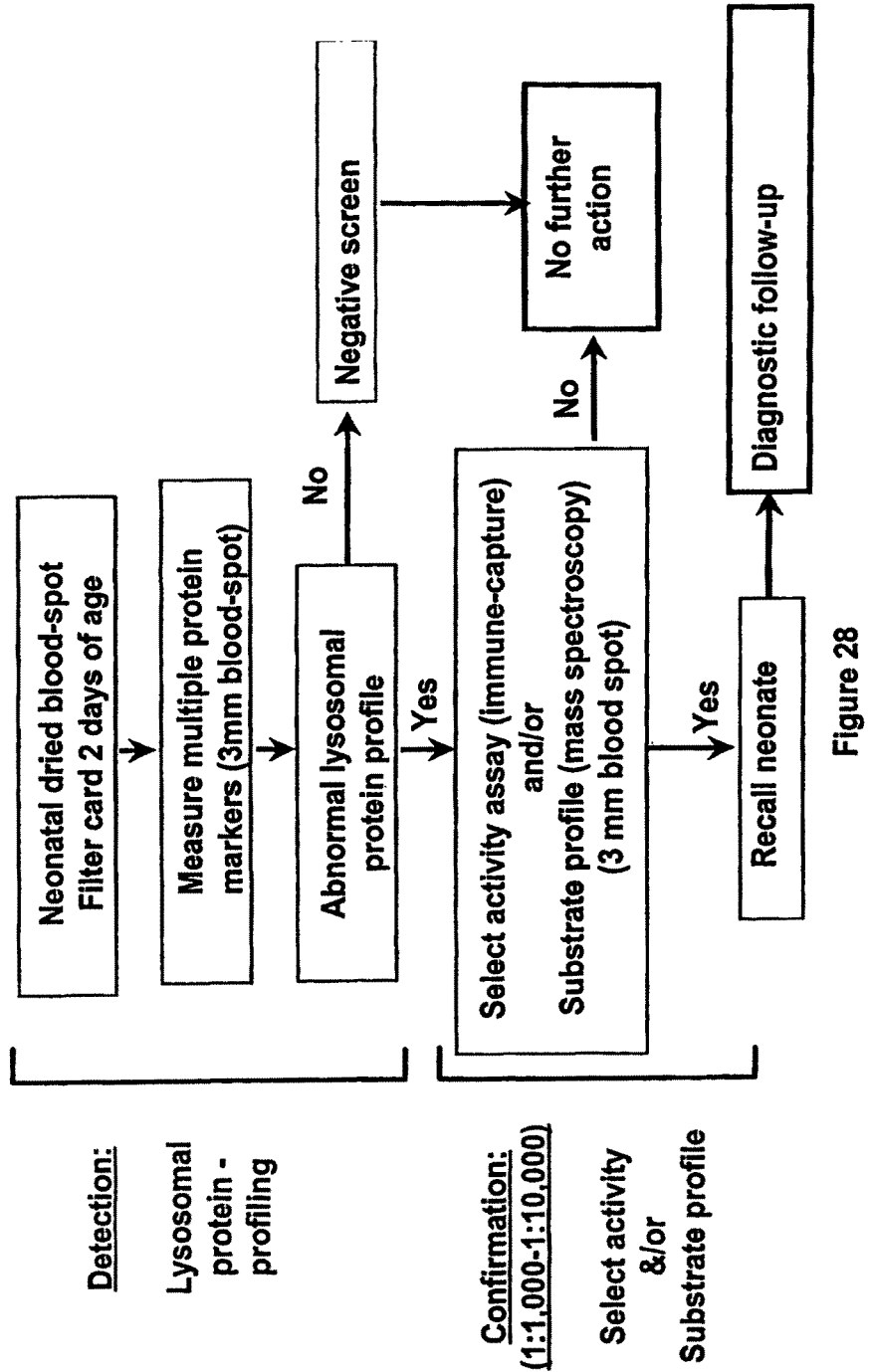
Figure 29:
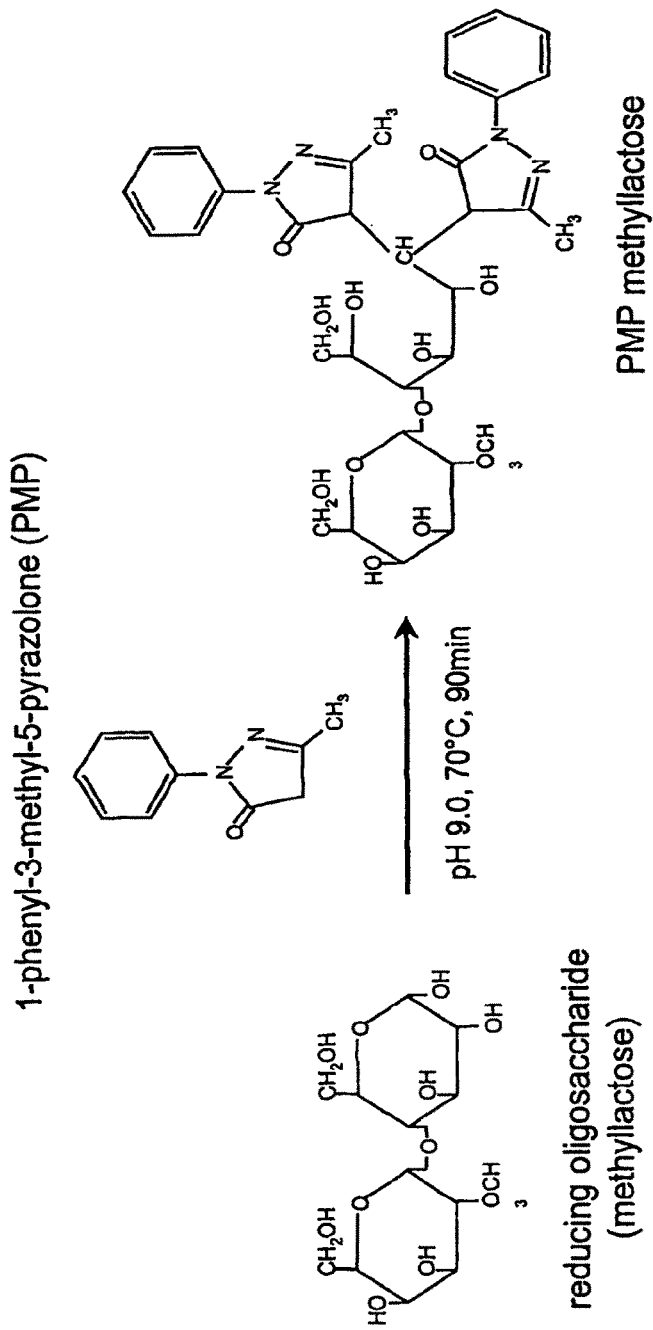
Figure 30:
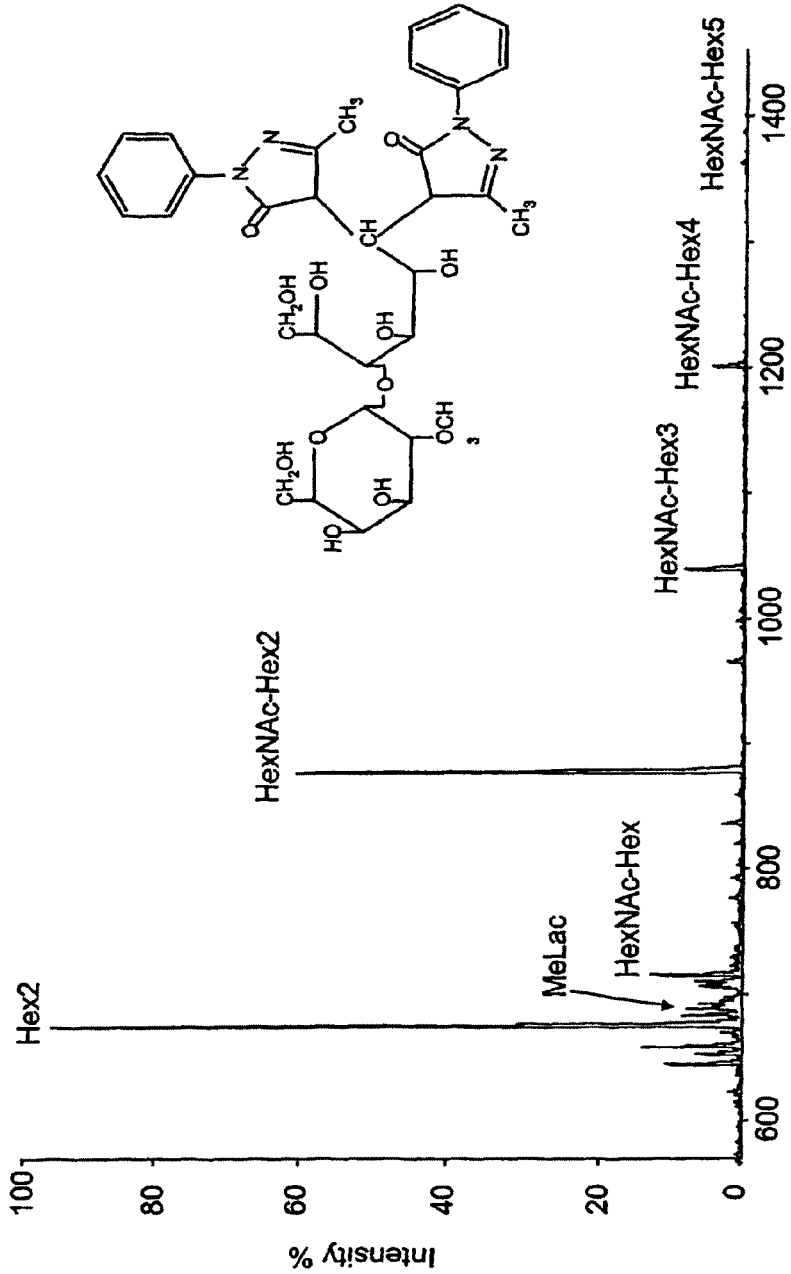
Figure 31:
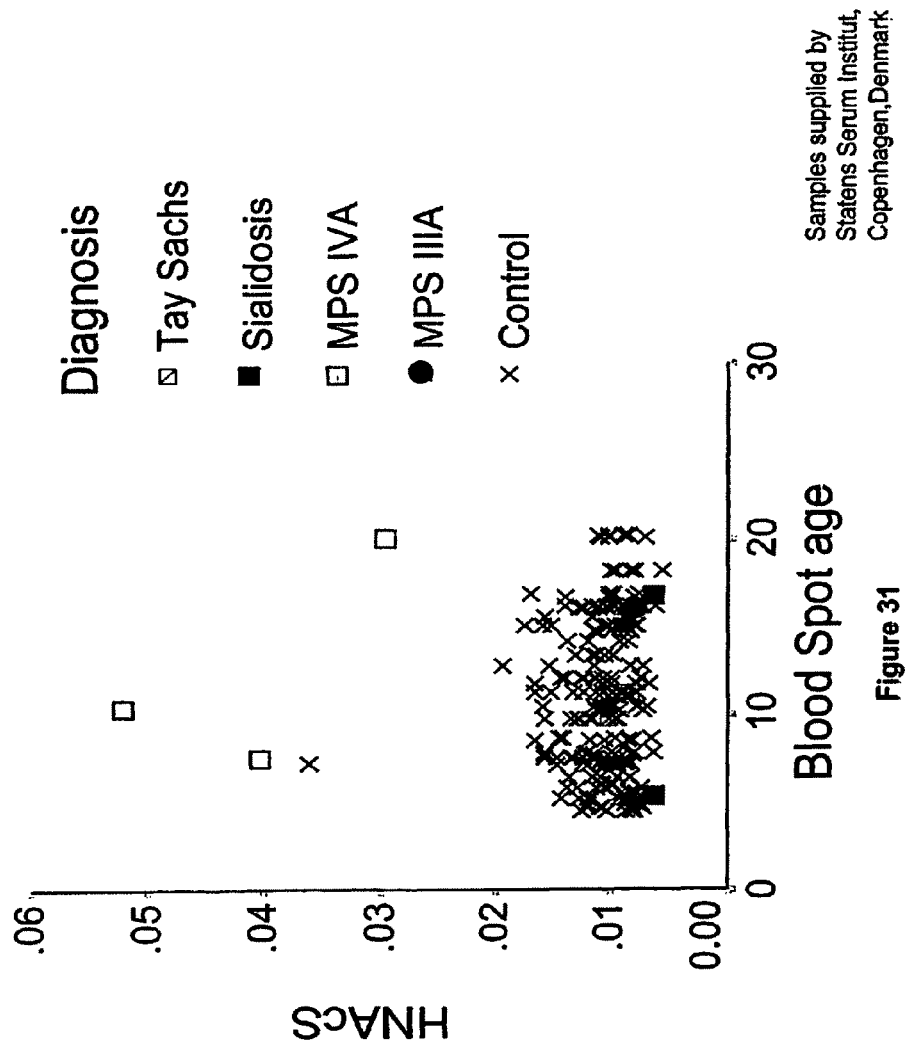
Figure 32:
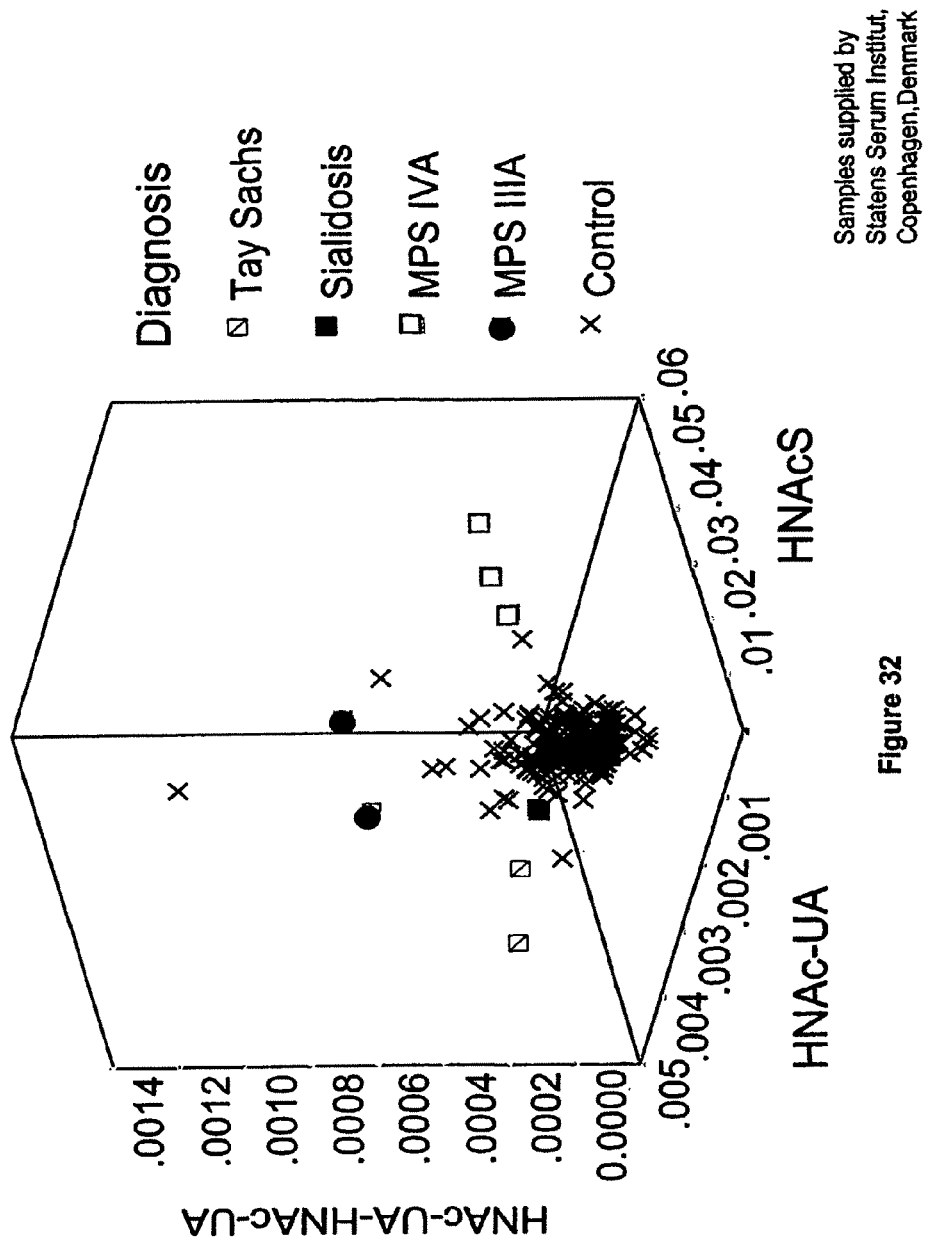

FIG. 20 shows target protein markers for LSD screening;

FIG. 21 shows the antibodies and bead regions used for the 7-plex assay;

FIG. 22 shows the calibration curves for each of the protein assays;

FIG. 23 shows the individual and average adult control protein values in the 7 plex assay obtained for each sample with the standard deviation, minimum and maximum of each group;

FIG. 24 shows the individual and average newborn protein values in the 7 plex assay for each sample with the standard deviation, minimum and maximum of each group;

FIG. 25 shows the Pearson correlation coefficient between each pair of protein analytes;

FIG. 26 shows the protein concentrations of the LSD individuals compared to adult control group;

FIG. 27 shows the protein concentrations of the LSD individuals compared to the newborn control group;

FIG. 28 shows the multiplex neonatal screening strategy for LSD;

FIG. 29 shows the derivatization of oligosaccharides for MS/MS analysis;

FIG. 30 shows MS/MS analysis of α-mannosidosis urine (Precursor ion scan of m/z 175);

FIG. 31 shows retrospective analysis of HNAcS in newborn blood spots vs blood spot age;

FIG. 32 shows retrospective analysis of HNAc-UA-HNAc-UA in newborn blood spots;

FIG. 33 shows a summary of retrospective analysis of newborn blood spots;

FIG. 34 shows protein markers for LSD screening using multiplex assays for LSD.

SUMMARY

Lysosomal Storage Disorders ("LSDs") represent a group of over 40 distinct genetic diseases that generally affect young children. Individuals that are affected with a LSD present a wide range of clinical symptoms that depend upon the specific disorder or a particular genotype involved. The present invention is generally related to a multiple screening diagnostic for LSD and related diseases. More particularly, this invention pertains to compounds, reagents, and methods for identifying and quantifying multiple target enzymes and proteins that are used to accurately diagnose a LSD. These target enzymes and proteins are naturally present in biological fluids or tissues of patients. The invention also pertains to a Multiplexing Bead Technology for simultaneous screening of specific LSD enzymes.

A first aspect of the current invention is a composition used for diagnosing a LSD. The composition comprises a capture antibody capable of binding a target antigen, and a microsphere having the capture antibody conjugated to the microsphere. The target antigen is a LSD associated biomolecule that comprises α-iduronidase, α-glucosidase, saposin C, LAMP-1, LAMP-2, β-glucosidase, α-galactosidase A, iduronate-2-sulphatase, N-acetylgalactosamine 4-sulphatase, galactose 6-sulphatase, acid sphingomyelinase, galactocerebrosidase, arylsulphatase A, saposin B, heparan-N-sulphatase, α-N-acetylglucosaminidase, acetylCoA: glucosamine N-acetyltransferase, N-acetylglucosamine 6-sulphatase, β-galactosidase, β-glucuronidase, aspartylglucosaminidase, acid lipase, β-hexosamindase A, β-hexosamindase B, GM2-acitvator, acid ceramidase, α-L-fucosidase, α-D-mannosidase, β-D-mannosidase, neuraminidase, phosphotransferase, phosphotransferase g-subunit, palmitoyl protein thioesterase, tripeptidyl peptidase I, cathespsin K, α-galactosidase B, or sialic acid transporter. The microsphere having the conjugated capture antibody has a diameter of about 5 μm and at least a first fluorophore and a second fluorophore. The first fluorophore being spectrally distinct from the second fluorophore. The composition may further comprise a detection antibody, wherein the detection antibody is capable of binding the target antigen, but is different from the capture antibody, and the detection antibody is conjugated to any detectable label known in the art (e.g. a fluorescent label).

A second aspect of the current invention comprises a protein profiling method for diagnosing a pre-clinical status, or a clinical status of a LSD. The method determines at least a first- and second-target antigen quantity from a target biological sample having an unknown clinical status of LSD. At least a first- and a second-reference antigen quantity are also determined from a reference biological sample having a known clinical status of LSD. The target antigens are LSD associated biomolecules that comprise α-iduronidase, α-glucosidase, saposin C, LAMP-1, LAMP-2, or other biomarkers associated with LSD. By calculating a target proportion between the first- and second-target antigen quantities, an adjusted target quantity can be assigned. Similarly, an adjusted reference quantity can be assigned by calculating a reference proportion between the first- and second-reference antigen quantities. The pre-clinical status or the clinical status of an LSD can then be determined by comparing a deviation of the adjusted target quantity to the adjusted reference quantity. In one specific embodiment, the target biological sample and the reference biological sample of this method are selected from a cellular extract, blood, plasma, or urine. Alternatively, the second target antigen and the second reference antigen comprise a biomarker indicator of cell number, organelle number, cell size, organelle size, cell volume, or organelle volume.

A third aspect of the current invention comprises a method for determining an amount of at least a first target antigen and at least a second target antigen indicative of a LSD in a target biological sample using a composition of capture antibody microspheres. The method comprises incubating at least a first capture antibody microsphere and at least a second capture antibody microsphere with the target biological sample forming a capture suspension. The first capture antibody microsphere and the second capture antibody microsphere are then recovered from the capture suspension. These first- and second-recovered microspheres are then hybridized with a first- and a second-detection antibody, respectively. The first recovered antibody microsphere and the second recovered antibody microsphere having a bound detection antibody can be detected when they are passed through an examination zone. Data is then collected that relates to one or more microsphere classification parameters, the presence or absence of the first- or second-detection antibody; and the amount of first- or second-detection antibody is quantified. In a specific embodiment, the target biological sample is selected from a cellular extract, blood, plasma, or urine. In another specific embodiment, the first target antigen and second target antigens are each α-iduronidase, α-glucosidase, saposin C or other biomarkers associated with a LSD. The second target antigen may also comprise an indicator of cell number, organelle number, cell size, organelle size, cell volume, or organelle volume.

A fourth aspect of the current invention comprises a method of detecting multiple LSD target antigens in a sample. The specific subset of LSD antigens comprises α-iduronidase, α-glucosidase, saposin C or other biomarkers associated with LSD. The method comprises exposing a pooled population of target capture microspheres to the sample. Each of the target capture microspheres have distinct subsets, and each distinct subset has: (i) one or more characteristic classification parameters that distinguishes one target capture microsphere of one subset from those of another target capture microsphere subset according to a predetermined discriminate microsphere function table, which includes fluorescence emission intensities; and (ii) a distinct capture antibody that can bind a specific subset of LSD antigens. After the pooled population of target capture microspheres has been exposed to the sample, the exposed pooled population of target capture microspheres is passed through examination zone. The identity and quantity of each specific subset of LSD target antigen of interest is determined, if present, in the sample by (i) collecting data relating to one or more subsets of target capture microsphere classification parameters that distinguishes one target capture antibody microsphere of one subset from those of another target capture antibody microsphere subset according to a predetermined discriminate function table, including the fluorescence emission intensities, (ii) collecting data relating to the presence or absence of a corresponding subset of specific LSD antigen, (iii) quantifying each corresponding subset of specific LSD antigen on each subset of capture antibody microsphere. In a specific embodiment, the method further comprises adding a pooled population of detection antibodies to the exposed pooled population of the target capture microspheres prior to passing the target capture microspheres through the examination zone.

DETAILED DESCRIPTION

Terms:

The term "a" or "an" as used herein in the specification may mean one or more. As used herein in the claim(s), when used in conjunction with the word "comprising", the words "a" or "an" may mean one or more than one. As used herein "another" may mean at least a second or more.

The term "animal," "subject," or "patient" as used herein may be used interchangeably and refers to any species of the animal kingdom. In preferred embodiments it refers more specifically to humans.

The term "biomolecule" as used herein is understood to represent the target molecule, such as a protein, an antibody, a metabolite, a DNA sequence, an RNA sequence; a biologic with activities used or measured for the purposes multiplexing and profiling of target biomolecules, or a combination thereof, for the composition and method of determining LSD, used in administering, monitoring, or modifying an LSD therapy.

The term "clinical status" as used herein refers to patients that are being studied or treated by physicians for a LSD.

The term "comprise," or variations such as "comprises" or "comprising," as used herein may be used to imply the inclusion of a stated element or integer or group of elements or integers, but not the exclusion of any other element or integer or group of elements or integers.

The term "fluorophore" as used herein refers to any fluorescent compound or protein that can be used to quantify the LSD antigens.

The term "normalize" as used herein refers to bringing a target, reference, or other samples into conformity with a standard, pattern, model, etc. For example, in one embodiment, urine samples from LSD patients and non-LSD patients were normalized by using a 1 µmol equivalent of creatinine from each sample.

The term "phenotype" as used herein refers to the manifest characteristics of an organism collectively, including anatomical and psychological traits, that result from both its heredity and its environment.

The term "preclinical status" as used herein refers to the period of a disease before any of the clinical symptoms appear.

The term "lysosomal storage disorder ("LSD") associated biomolecule" as used herein refers to any biomolecule that has been linked to any LSD. In preferred embodiments, a LSD associated biomolecule includes, but is not limited to: α-iduronidase, α-glucosidase, saposin C, LAMP-1, LAMP-2, β-glucosidase, α-galactosidase A, iduronate-2-sulphatase, α-iduronidase, N-acetylgalactosamine 4-sulphatase, galactose 6-sulphatase, acid sphingomyelinase, galactocerebrosidase, arylsulphatase A, saposin B, heparan-N-sulphatase, α-N-acetylglucosaminidase, acetylCoA: glucosamine N-acetyltransferase, N-acetylglucosamine 6-sulphatase, β-galactosidase, β-glucuronidase, aspartylglucosaminidase, acid lipase, β-hexosamindase A, β-hexosamindase B, GM2-acitvator, acid ceramidase, α-L-fucosidase, α-D-mannosidase, β-D-mannosidase, neuraminidase, phosphotransferase, phosphotransferase g-subimit, palmitoyl protein thioesterase, tripeptidyl peptidase cathespsin K, α-galactosidase B, or sialic acid transporter. As shown below, Table 1 indicates some enzyme deficiencies for LSDs.

TABLE 1

Enzymes deficient in some common lysosomal storage disorders

| Disease | Clinical Phenotype | Enzyme Deficiency | Australian Prevalence |
|---|---|---|---|
| Gaucher disease types I/II/III | Gaucher disease | Glucocerebrosidase (β-glucosidase) | 1 in 57,000 |
| Cystinosis | | Cystine transporter | 1 in 192,000 |
| Fabry disease | Fabry disease | α-Galactosidase A | 1 in 117,000 |
| Glycogen storage disease II | Pompe disease | α-Glucosidase | 1 in 146,000 |
| Mucopolysaccharidosis type I | Hurler/Scheie syndrome | α-L-Iduronidase | 1 in 88,000 |
| Mucopolysaccharidosis type II | Hunter syndrome | Iduronate-2-sulphatase | 1 in 136,000 |
| Mucopolysaccharidosis type VI | Maroteaux-Lamy syndrome | N-acetylgalactosamine 4-sulphatase | 1 in 235,000 |
| Mucopolysaccharidosis type IVA | Morquio syndrome | Galactose 6-sulphatase | 1 in 169,000 |
| Niemann-Pick disease types A/B | Niemann-Pick disease | Acid sphingomyelinase | 1 in 248,000 |
| Globoid cell leucodystrophy | Krabbe disease | Galactocerebrosidase | 1 in 201,000 |
| Metachromatic leucodystrophy | | Arylsulphatase A | 1 in 92,000 |
| Metachromatic leucodystrophy | | Saposin B | |
| Mucopolysaccharidosis type IIIA | Sanfilippo syndrome | Heparan-N-sulphatase | 1 in 114,000 |
| Mucopolysaccharidosis type IIIB | Sanfilippo syndrome | α-N-Acetylglucosaminidase | 1 in 211,000 |
| Mucopolysaccharidosis type IIIC | Sanfilippo syndrome | AcetylCoA: N-acetyltransferase | 1 in 1,407,000 |
| Mucopolysaccharidosis type IIID | Sanfilippo syndrome | N-Acetylglucosamine 6-sulphatase | 1 in 1,056,000 |
| Mucopolysaccharidosis type IVB | Morquio syndrome | β-Galactosidase | |
| Mucopolysaccharidosis type VII | Sly | β-Glucuronidase | 1 in 2,111,000 |
| Niemann-Pick disease type C1 | Niemann-Pick disease | Cholesterol trafficking | 1 in 211,000 |
| Niemann-Pick disease type C2 | Niemann-Pick disease | Cholesterol trafficking | 1 in 2,111,000 |
| Aspartylglucosaminuria | | Aspartylglucosaminidase | |
| Cholesterol ester storage disease | Wolman disease | Acid lipase | 1 in 528,000 |
| GM1-Gangliosidosis types I/II/III | | β-Galactosidase | 1 in 384,000 |
| GM2-Gangliosidosis type I | Tay Sachs disease | β-Hexosaminidase A | 1 in 201,000 |
| GM2-Gangliosidosis type II | Sandhoff disease | β-Hexosaminidase A & B | 1 in 384,000 |
| GM2-Gangliosidosis | | GM2-activator deficiency | |
| Farber Lipogranulomatosis | Farber disease | Acid ceramidase | |
| Fucosidosis | | α-L-Fucosidase | >1 in 2,000,000 |
| Galactosialidosis types I/II | | Protective protein | |
| α-Mannosidosis types I/II | | α-D-Mannosidase | 1 in 1,056,000 |
| β-Mannosidosis | | β-D-Mannosidase | |
| Mucolipidosis type I | Sialidosis types I/II | Neuraminidase | |
| Mucolipidosis types II/III | I-cell disease; pseudo-Hurler polydystrophy | Phosphotransferase | 1 in 325,000 |
| Mucolipidosis type IIIC | | Phosphotransferase g-subunit | |
| Mucolipidosis type IV | | Unknown | |
| Multiple sulphatase deficiency | | Multiple sulphatases | 1 in 1,407,000 |
| Neuronal Ceroid Lipofuscinosis, CLN1 | Batten disease | Palmitoyl protein thioesterase | |
| Neuranal Ceroid Lipofuscinosis, CLN2 | Batten disease | Tripeptidyl peptidase I | |
| Neuronal Ceroid Lipofuscinosis, CLN3 | Vogt-Spielmeyer disease | Protein function not known | |
| Neuronal Ceroid Lipofuscinosis, CLN5 | Batten disease | Protein function not known | |
| Neuronal Ceroid Lipofuscinosis, CLN8 | Northern Epilepsy | Protein function not known | |
| Pycnodysostosis | | Cathepsin K | |
| Sialic acid storage disease | Schindler disease | α-Galactosidase B | |
| Sialic acid storage disease | Sialuria; salla disease | Sialic acid transporter | 1 in 528,000 |

Prevalence figures quoted from Miekle et al., *JAMA* 281: 249-254 (1999). Prevalence and ratio of lysosomal storage disorders may vary from country to country The term "reference quantity" as used herein refers to a known, normalized amount of a LSD biomarker in a biological fluid. The reference quantity is determined from an animal, or group of animals having a defined clinical status, preclinical status, or phenotype of a LSD disease. The reference quantity may refer to a table compiled from various animals or groups of animals having correlations between relative amounts of LSD biomarkers in a biological fluid, and a known clinical status, preclinical status, or phenotype.

Lysosomal Storage Disorders

The LSD's represent a group of over 40 distinct genetic diseases that generally affect young children. Patients are usually born without the visible features of a LSD, but early stage symptoms can quickly develop into a progressive clinical concern. Although some effective LSD therapies have been developed, it is paramount that therapy be started as soon as the LSD has been diagnosed. Unfortunately, a clinical diagnosis of a LSD often requires multiple visits to a range of specialists requiring time-consuming, invasive, complex, inconvenient; and expensive assays. The current process for an accurate diagnosis of LSD for a patient not having a family history of LSD can take months to years, which is unacceptable when effective LSD therapies are needed earlier.

It is generally recognized that the accumulation of storage materials in the lysosomes of LSD affected individuals will increase from approximately 1% to as much as 50% of the total cellular volume. Certain lysosomal proteins are present at altered levels in the LSD affected individuals (Meikle et al., 1997; Hua et al., 1998), as indicated in FIGS. 1-6. The values for the individual immunoassays in plasma samples were determined as follows and shown in FIGS. 1-6. Unless stated otherwise all regents were of analytical grade and were obtained from Sigma Chemical Company, MO USA. Preparation of recombinant proteins, antibodies and calibration standards for Lamp-1 and saposin C. Recombinant Lamp-1 (minus tail) was isolated from CHO-K1 cells as detailed in Isaac et al [Isaac E L, Karageorgous L E, Brooks D A, Hopwood J J and Meikle P J. Experimental Cell Research 2000, 254: 204-209]. Recombinant Saposin C was a gift from Dr G A Grabowski and was prepared by the method of Qi and Grabowski [Qi T L and Grabowski G A J Biol Chem 1994, 269: 16746-16753].

The anti Lamp-1 monoclonal antibody (BB6) was generated using intact Lamp-1 protein by the method of Carlsson and Fukada [Carlsson S R and Fukada M JBC (1989) 264 (34): 20526-20531] and 7132 (anti Saposin C) monoclonal antibody was produced using the recombinant protein by the method described in [Zola H and Brooks D. Techniques for the production and characterization of monoclonal hybridoma antibodies. In: Hurrell J G R, ed. Monoclonal hybridoma antibodies: techniques and applications. Boca Raton, Fla.: CRC Press, 1982:1-57]. Polyclonal antibodies were generated for both Lamp-1 and Saposin C by immunizing separate rabbits with 200 µg of each recombinant protein per inoculation (four inoculations in total) based upon the method of Leonova et al, 1996, [JBC 271:17312-20]. All antibodies were purified using 5 ml Hitrap™ Protein G affinity column (Pharmacia, Uppsala, Sweden). The polyclonal antibodies were affinity, purified further by column chromatography using their respective recombinant proteins coupled to Affi-Gel® 10 Gel (Bio-Rad #153-6046, CA, USA) according to manufacturers instructions.

Blood spot calibrators containing final concentrations of 2000, 1000, 500, 250, 62.5 and 0 µg/L for Lamp-1 and saposin C' were prepared as detailed in Umapathysivam et al [Umapathysivam K, Whittle A M, Ranieri E, Binefloss C, Ravenscroft E M, van Diggelen O P, Hopwood J J and Meikle P J Clin Chem 46(9): 1318-1325 2000]. Two blood spot controls containing low (Lamp-1 400 µg/L; saposin 200 µg/L) and high (Lamp-1 800 µg/L; saposin C 500 µg/L) protein concentrations were similarly prepared.

Quantification of Lamp-1 and Saposin C in Dried Blood Spots Containing EDTA.

Lamp-1 and Saposin C were measured in dried blood spots using one step three tier, time-delayed fluorescence immunoassays. Microtiter plates (Labsytems, Helsinki, Finland #95029180) were coated with either BB6 or 7B2 at a concentration of 5 µg/L in 0.1 mol/l NaHCO3, pH 8.3 and incubated covered for approximately 16 hrs at 4° C. Plates were washed twice with wash buffer (0.25 mol/lNaCl, 0.02 mol/l Tris containing 0.005% TWEEN® 20 surfactant (BDH, Poole, England) and 0.002% Thiomerosal, pH7.8) Non-specific binding sites on the plates were blocked by the addition of 100 µl of 0.25M NaCl, 0.02M Tris containing 0.5% skim milk powder (Diploma, Bonlac Foods, Victoria, Australia), pH 7.8, per well. After a two hour incubation at room temperature, the microtiter plates were washed twice with 0.25M NaCl, 0.02M Tris pH 7.8 and tapped dry before being lyophilized and stored desiccated at 4° C. prior to use.

Standard calibrators, controls and patient dried blood spots were placed in duplicate into the coated microtiter wells with 200 µl of either polyclonal antibody diluted in assay buffer (0.15 mol/l NaCl, 0.05 mol/L Tris, 20 µmol/L Diethylene triamine-penta-acetic acid, containing 0.01% TWEEN® 40 surfactant, 0.5% bovine serum albumin (A-9647), 0.05% bovine γ-globulin (G-7516), and 0.05% sodium azide, pH 7.8). The antibodies were used at a final concentration of 200 µg/L and 400 µg/L for the anti-Lamp-1 and anti saposin C polyclonal respectively. The plates were covered and incubated at room temperature for one hour with shaking, then placed overnight at 4° C., followed by an hour incubation with shaking at room temperature. The blood spots were removed by suction and the plates washed six times with wash buffer. After dilution in assay buffer to final concentration of 0.1 µg/ml, 100 µl of anti rabbit europium labeled antibody (Wallac, Finland #AD0105), was added to every well and incubated for one hour at room temperature with shaking. After washing the plates a final six times with wash buffer, 200 µl of DELFIA® Enhancement solution (Wallac, Finland) was added per well and the plates incubated at room temperature for ten minutes with shaking. Fluorescence was measured on a DELFIA® 1234 Research Fluorometer (Wallac, Finland). The concentrations of Lamp-1 and Saposin C in the blood spots were calculated using spline fit curves generated by Multicalc Data Analysis software (version 2.4 Wallac, Finland)

Figure 1:
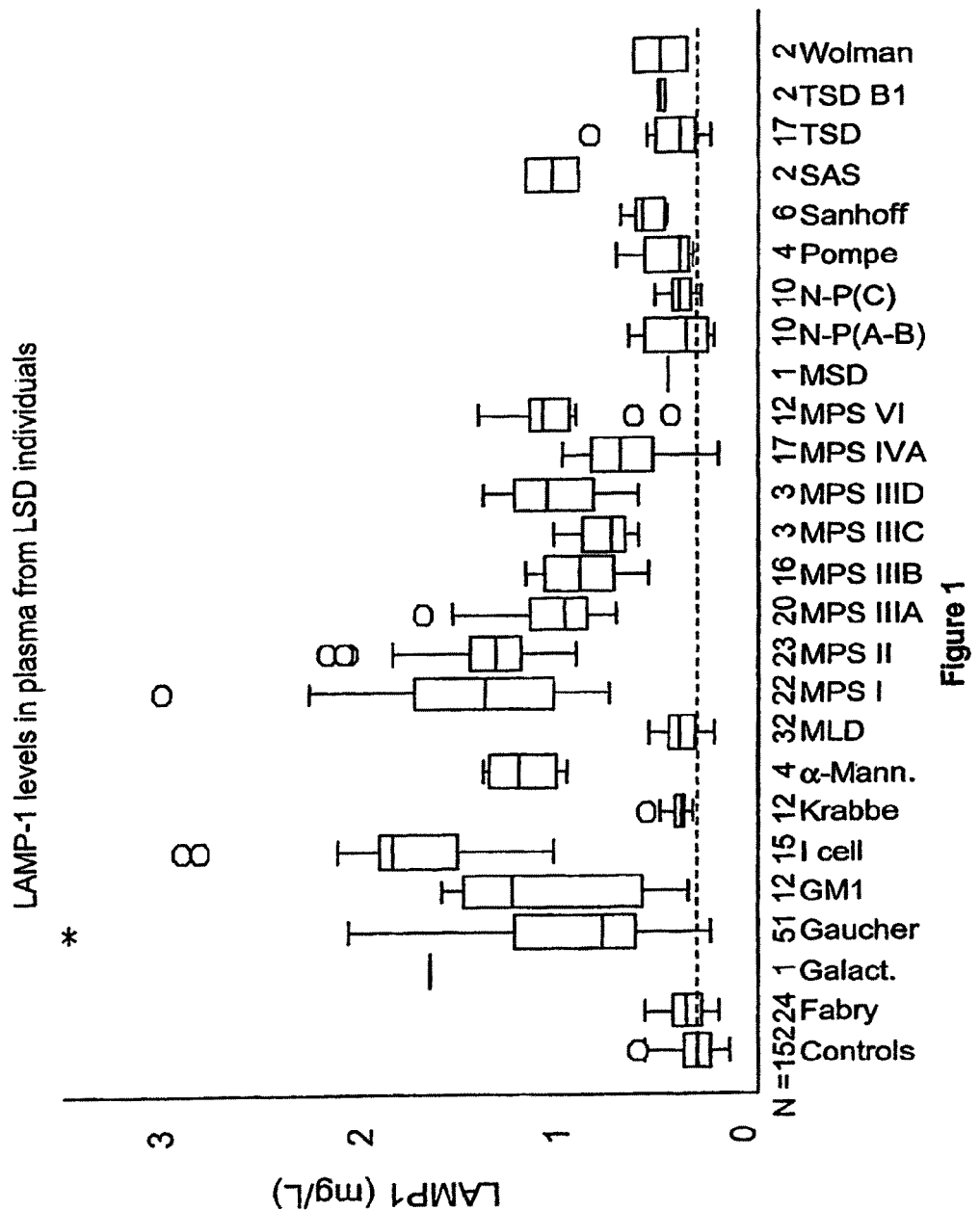
Figure 2:
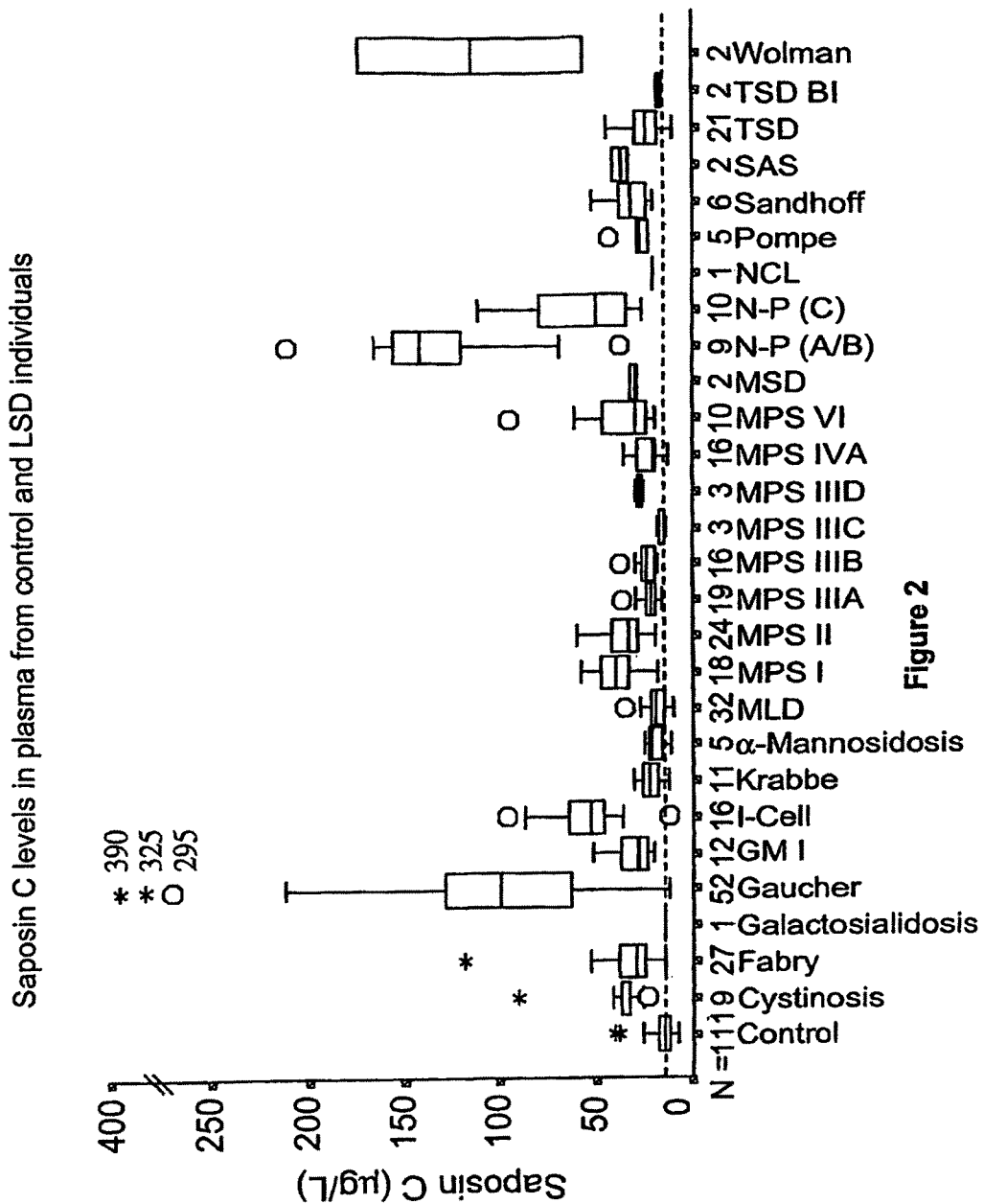
Figure 3:
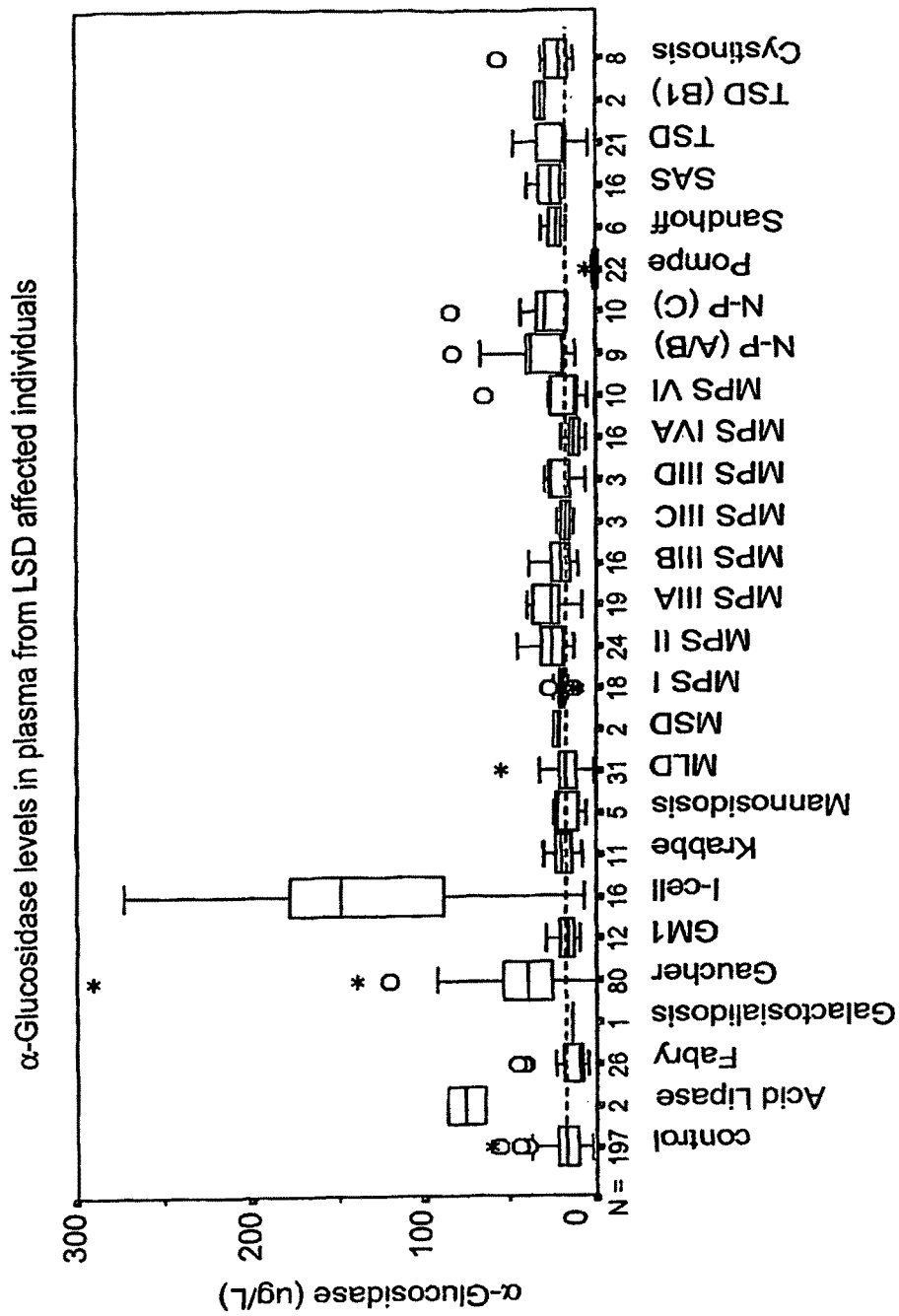

FIG. 1 shows the LAMP-1 levels in plasma from LSD individuals that are indicated by the box length being the interquartile range that covers 25th to 75th percentile. FIG. 2 shows saposin C levels in plasma from LSD individuals wherein the box length is the inter-quartile range that covers 25th to 75th percentile. FIG. 3 shows α-Glucosidase in plasma from LSD affected individuals, wherein the box length is the inter-quartile range that covers 25th to 75th percentile.

Figure 4:
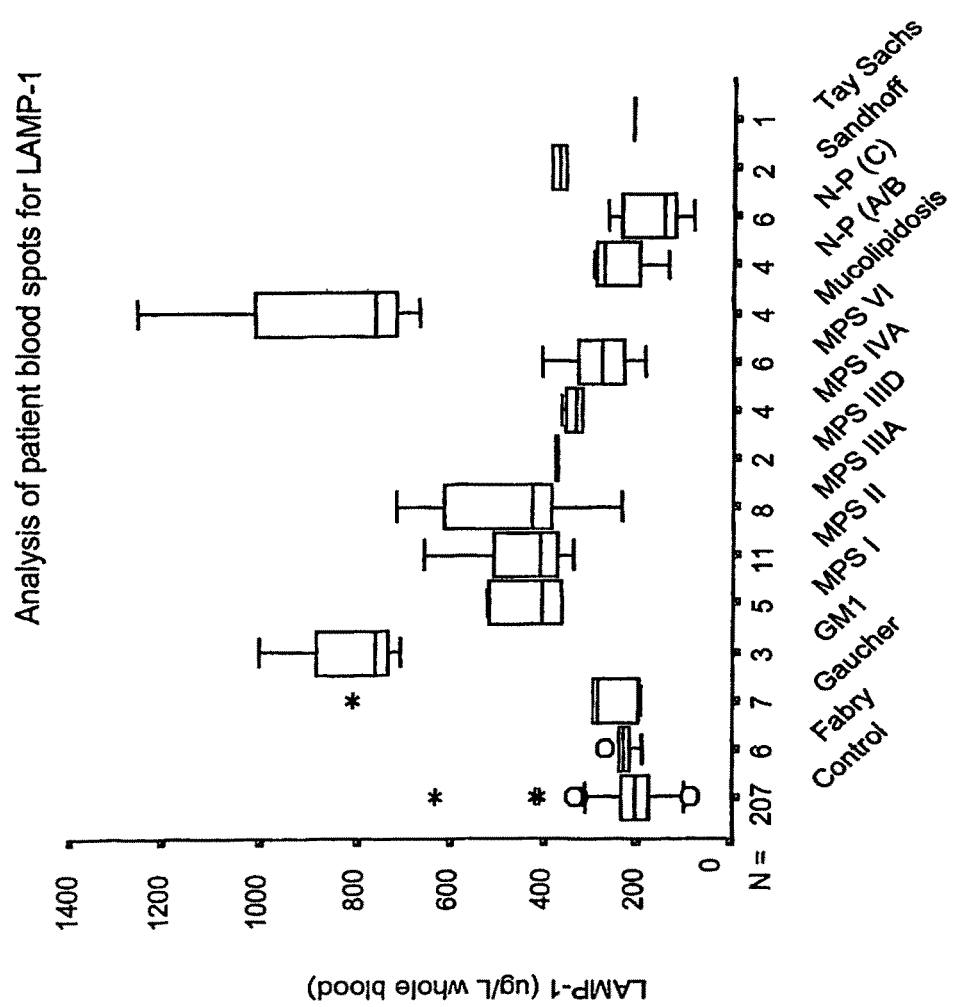
Figure 5:
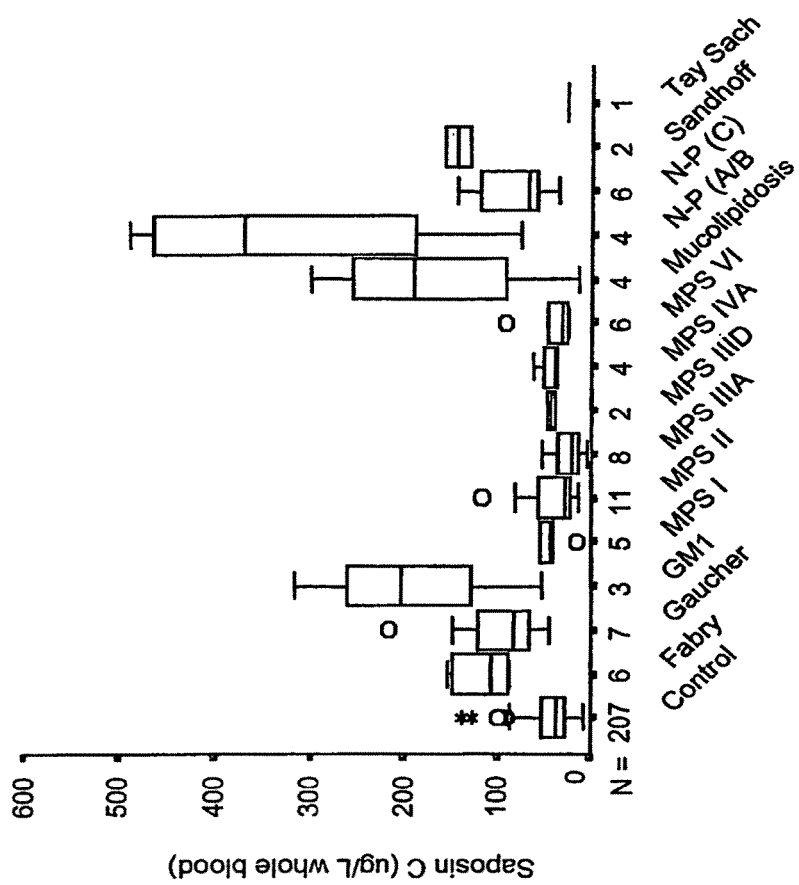
Figure 6:
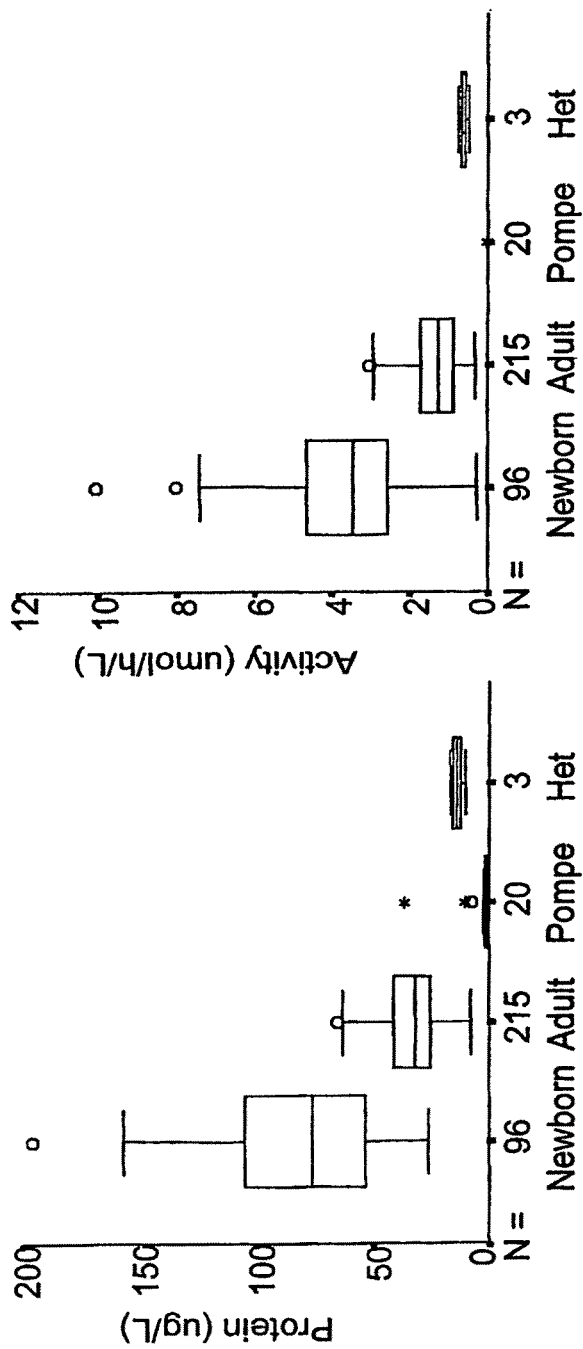
Figure 7:
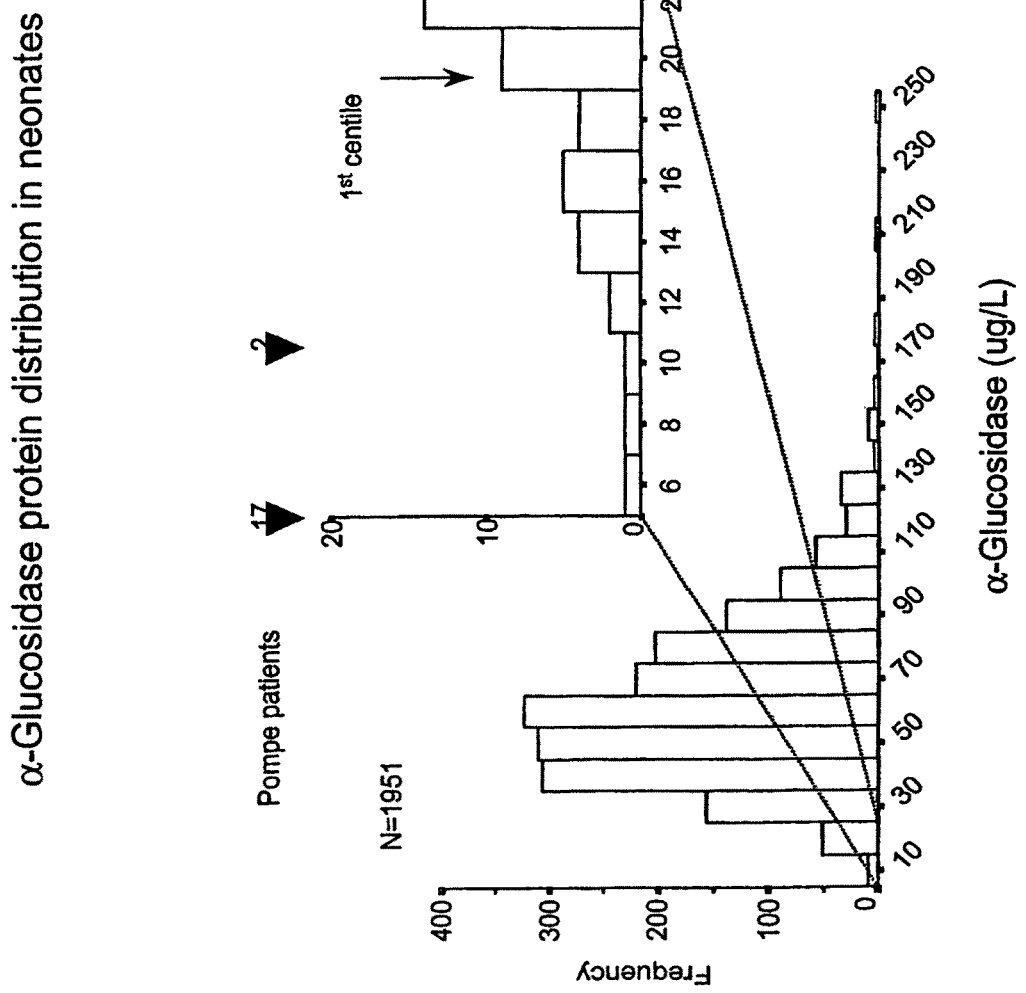
FIG. 7 shows α-Glucosidase protein distribution in neonates.
Figure 8:
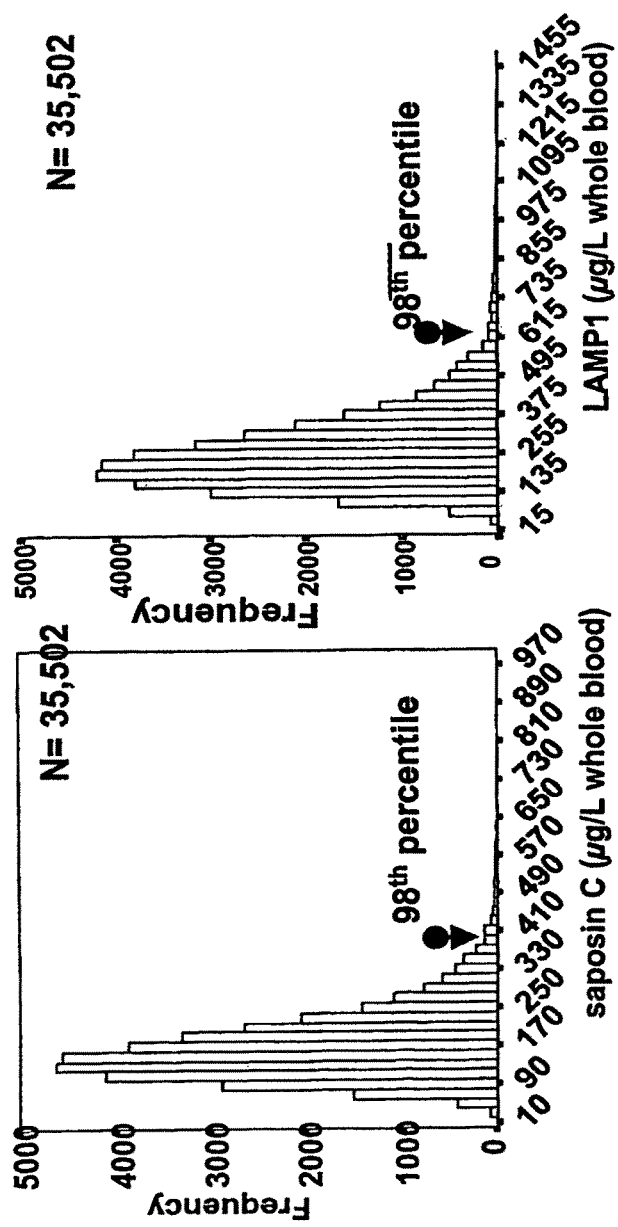
FIG. 8 shows the newborn population distribution of LAMP-1 and saposin C
Figure 9:
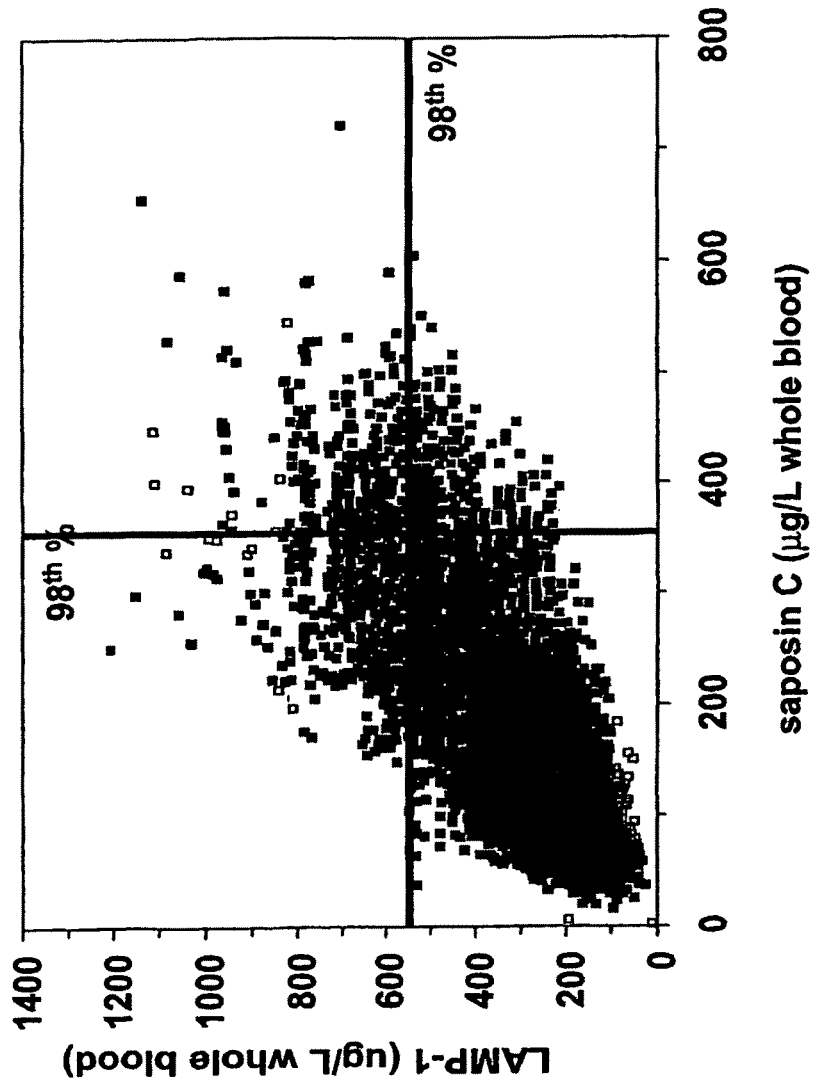
FIG. 9 shows target populations representing each LSD of interest analyzed.

Target enzymes can also be detected by individual immunoassays in dried blood spots, as indicated in FIG. 4, FIG. 5, and FIG. 6. For example, FIG. 4 shows analysis of patient blood spots for LAMP-1, wherein the box length is the inter-quartile range that covers 25th to 75th percentile. FIG. 5 shows Analysis of patient blood spots for saposin C wherein the box length is the inter-quartile range that covers 25th to 75th percentile. FIG. 6 shows α-Glucosidase protein/activity determination in dried blood spots, wherein the box length is the inter-quartile range that covers 25th to 75th percentile. FIG. 7 shows α-Glucosidase protein distribution in neonates. FIG. 8 shows the newborn population distribution of LAMP-1 and saposin C, and FIG. 9 shows target populations representing each LSD of interest analyzed.

Although certain lysosomal target proteins are present at altered levels in the affected individuals, the current individual screening assays may be inaccurate due to variations among individual samples. For example, a given sample is assumed to contain an average number of lysosomes or white blood cells ("WBC"), however variations in these values between individual samples are not typically considered. Thus, variations in an individual having a deficiency in a particular LSD biomolecule (e.g. lysosomal target protein), but also having an unusually high WBC count or high numbers of lysosomes in the test sample may return an assay result that is consistent for individuals that do not have a LSD. Consequently, if WBC or high numbers of lysosomes were controlled in the sample preparation a large inaccuracy could be avoided, and a proper diagnosis could be made during the first round of LSD screening.

Determining the quantities of multiple target enzymes increases the accuracy of diagnosing a specific LSD as compared to any single assay. For example, using immunoquantification assays directed toward identifying the levels of the lysosome-associated membrane proteins ("LAMPs"), such as LAMP-1 or LAMP-2, in an "at-increased-risk" group will identify up to 65% of LSD affected individuals. However, the combination of LAMP's with one of the saposins increases identification of LSD affected individuals to approximately 85%. Therefore, a method to identify two or more biomarkers simultaneously would increase the accuracy of LSD diagnosis and reduce the time and cost for each assay. A Multiplexing Bead Technology is used to simultaneously detect specific at least 2 LSD target antigens is described below or in Table 1.

Example 1

Multiplexing Bead Technology and Target LSD Proteins

The Multiplexing Bead Technology is built around 3 core technologies. The first is the family of fluorescently dyed microspheres having bound biomolecules. The second is a flow cytometer with 2 lasers and associated optics to measure biochemical reactions that occur on the surface of the microspheres, and the third is a high-speed digital signal processor to efficiently manage the fluorescent output. Bio-Rad (Hercules, Calif.), provides a commercially available protein array system called the "Bio-Plex™". The BioPlex™ protein array system includes fluorescently dyed microspheres, a flow cytometer with 2 lasers and associated optics, and a high-speed digital signal processor. However, neither the Bio-Plex™ protein array system nor any other commercially available systems include any specific biomolecules, methods, compounds, or reagents needed for the simultaneous screening of specific LSD enzymes.

The Bio-Plex™ protein array system uses multiplexing technology to enable the simultaneous quantitation of up to 100 different analytes. This technology uses polystyrene microspheres internally dyed with differing ratios of 2 spectrally distinct fluorophores. Each fluorophore can have any of 10 possible levels of fluorescent intensity, thereby creating a family of 100 spectrally distinct bead sets. In a preferred embodiment, the dyed microspheres are conjugated with monoclonal antibodies specific for a target LSD protein or peptide thereof. Although not wanting to be bound by theory, each of the 100 spectrally distinct bead sets can contain a capture antibody specific for a unique LSD target protein. In a multiplexed Bio-Plex™ assay, LSD antibody-conjugated beads are allowed to react with the sample and a secondary LSD antibody, or a detection LSD antibody in a microtiter plate well to form a capture sandwich immunoassay. FIG. 10 shows a drawing of a complete microsphere capture sandwich immunoassay having a polystyrene microsphere (110) with 2 spectrally distinct fluorophores; the target LSD capture antibody (120) bound to the microsphere; a unique LSD target protein or target antigen (130) bound to the target LSD capture antibody; a detection LSD antibody (140); and a detection molecule (150). Once the complete microsphere capture sandwich immunoassay has formed in solution, the immunoassay solution is then drawn into the Bio-Plex™ array reader, which illuminates and reads the sample. Although not wanting to be bound by theory, there are many enzyme deficiencies specific for a particular LSD, and some of these enzymes are shown in Table 1. Specific capture antibodies, and detection antibodies for the target compounds are available for specific LSD's, as shown in FIG. 11. Additional capture antibodies and detections antibodies include: β-glucosidase; α-galactosidase A; iduronate-2-sulphatase; α-iduronidase; N-acetylgalactosamine 4-sulphatase; galactose 6-sulphatase; acid sphingomyelinase; galactocerebrosidase; arylsulphatase A; saposin B; heparan-N-sulphatase; α-N-acetylglucosaminidase; acetylCoA: glucosamine N-acetyltransferase; N-acetylglucosamine 6-sulphatase; β-galactosidase; β-glucuronidase; aspartylglucosaminidase; acid lipase; β-hexosamindase A; β-hexosamindase B; GM2-activator; acid ceramidase; α-L-fucosidase; α-D-mannosidase; β-D-mannosidase; neuraminidase; phosphotransferase; phosphotransferase g-subunit; palmitoyl protein thioesterase; tripeptidyl peptidase I; cathespsin K; α-galactosidase B; sialic acid transporter.

When a red diode "classification" laser (635 nm) in the Bio-Plex™ array reader illuminates a dyed bead, the bead's fluorescent signature identifies it as a member of one of the 100 possible bead sets. Bio-Plex™ Manager software correlates each bead set to the assay reagent that has been coupled to it (for example, a first LSD capture antibody coupled to bead set #22, and a second LSD capture antibody coupled to bead set #42). In this way the Bio-Plex™ protein array system can distinguish between the different assays combined within a single microtiter well. A green "reporter" laser (532 nm) in the array reader simultaneously excites a third fluorescent dye (phycoerythrin, "PE") bound to the detection LSD antibody in the assay. Although not wanting to be bound by theory, the amount of green fluorescence is proportional to the amount of target analyte captured in the immunoassay. Extrapolating the captured amount of target analyte to a standard curve allows quantitation of each LSD analyte in the sample. The digital signal processing algorithms provide simultaneous real-time data acquisition of classification and reporter signal output from thousands of beads per second, supporting up to 100× 96=9,600 analyte measurements from each 96-well plate.

Example 2

Designing and Producing LSD Target Microspheres

The BioPlex Protein Array System was used as one embodiment to demonstrate the type and nature of the reagents necessary for a LSD multiplex diagnostic assay. Four target proteins (e.g. LAMP-1, α-iduronidase, α-glucosidase, and saposin C) were used to design target capture microspheres and target reporter antibodies.

The monoclonal capture antibody for LAMP-1 was BB6 developed and provided by Sven Carlsson (Carlsson et al., 1989). The monoclonal reporter antibody for α-glucosidase (43D1) was obtained from Pharming, Inc. and has been described (Fransen et al., 1988). The polyclonal reporter antibody for LAMP-1, the rabbit polyclonal reporter antibody for saposin C, the sheep polyclonal capture antibody for α-glucosidase, and the monoclonal capture antibody ("7B2") for saposin C were prepared within the Lysosomal Diseases Research Unit at the WCH in Adelaide, Australia using standard techniques, known in the art, and briefly described below. The availability and production of specific monoclonal and polyclonal antibodies are know to one of ordinary skill in the art. Production of the specific antibodies uses in the current examples are given below:

Polyclonal Antibodies.

Sheep polyclonal antibody was produced against recombinant proteins. A sheep was injected sub-cutaneously with 2 mg of protein in 1 ml, of an emulsion of phosphate buffered saline (pH 7.4) and complete Freunds adjuvant, followed by four booster injections (2 mg each) with incomplete Freunds adjuvant, each three weeks apart. One week after the last injection the sheep was bled out and serum collected. Rabbit polyclonal antibody was produced in the same manner, except 0.2-1.0 mg of protein was used per immunisation. Sheep polyclonal antibody was purified on a 5 ml Hitrap™ Protein G affinity column (Pharmacia Biotech, Uppsala, Sweden) followed by an affinity column prepared from the recombinant protein used for the immunisation. Recombinant protein affinity columns were prepared by coupling 5 mg of the recombinant protein to 2.5 mL of Affi-gel 10 (Bio-Rad, Hercules, Calif., USA) as per manufacturer's instructions.

Briefly, 5 ml of sheep serum was diluted with 5 ml of phosphate buffered saline (pH 7.4) and centrifuged (2200 g, 10 min, 4° C.). The centrifuged serum was passed through a 0.2 µm filter, and then loaded on to the Protein G column at a flow rate of 0.5 mL/min. The column was washed with phosphate buffered saline, pH 7.4 and the antibody eluted with 0.1 mol/L $H_3PO_4$/$NaH_2PO_4$, pH 2.5 and immediately neutralised by adding 1.0 mol/L $Na_2HPO_4$ ($1/10^{th}$ vol). The protein content was estimated by absorbance at 280 nm (absorbance=1.4 for 1.0 g/L of protein). The eluate was diluted four fold and then loaded on to the appropriate recombinant protein affinity column at the same flow rate. The column was washed and eluted as described for the Protein G column.

Monoclonal Antibodies.

Monoclonal antibodies were produced in Balb/C mice using standard immunisation protocols (Harlow et al., 1988). Mice were immunised with recombinant enzyme using established protocols. Plasma cells from these immunised mice were fused with P3.653 myeloma cells (Zola et ed., 1982) and the resulting hybridoma cell lines screened for antibodies against the recombinant protein by direct FT ISA (Harlow et al., 1988). Monoclonal antibodies were purified from cell culture supernatants by ammonium sulfate precipitation followed by affinity purification on Hitrap™ Protein G affinity column (Pharmacia Biotech, Uppsala, Sweden).

Coupling Antibodies to Microspheres.

The target capture antibodies were Coupled to Bio-Rad carboxylated ("COOH") beads as follows: anti-LAW-1 to bead #(17), anti-saposin C to bead #(19), and anti-α-glucosidase to bead #(21). The coupling of the target capture antibodies to the polystyrene microspheres was performed using the BioRad bead coupling kit (Catalog number 171-406001, BioRad, Hercules, Calif.). The Bio-Plex™ amine coupling kit includes 4 ml bead wash buffer, 85 ml bead activation buffer, 135 ml PBS, pH 7.4, 10 ml blocking buffer, 25 ml storage buffer, 105 ml staining buffer, 40 coupling reaction tubes. The Bio-Plex™ amine coupling kit provides the buffers necessary to covalently couple 6-150 kD proteins to 5.5 µm dyed carboxylated polystyrene beads in under 5 hr. The covalent couple of the target capture antibody to the carboxylated polystyrene bead is achieved via carbodiimide reactions involving the protein primary amino groups and the carboxyl functional groups bound on the surface of polystyrene beads. The covalent attachment is permanent, leaving no unbound protein after cleanup, even after months of storage. The protein-coupled beads can then be used in multiplex protein-protein binding studies or in the development of multiplex assays that can be analyzed with the Bio-Plex™ protein array system. The bead yield per coupling reaction is approximately 80%, or enough protein-coupled beads for two 96-well microtiter plates using 5,000 beads per well.

Once the coupling reaction was completed, the target capture antibody-coupled beads were enumerated and the efficiency of the protein coupling reaction was validated, according to the manufacturer's protocol with modifications. In this procedure, the protein-coupled beads were reacted with a phycoerythrin ("PE")-labeled antibody that binds to the coupled protein, which was then analyzed using the Bio-Plex™ protein array system. This procedure was performed by reacting the beads with a PE-labeled antibody. Alternatively, a reaction using a biotinylated antibody followed by streptavidin-PE may be used. Although not wanting to be bound by theory, the intensity of the fluorescent signal of this reaction is directly proportional to the amount of protein on the surface of the beads. A successful coupling typically yields a mean fluorescent intensity ("MFT") signal that is greater than 2,000. The protein coupling validation procedure provided a rapid relative assessment of the amount of protein coupled to the beads, but could not verify the functionality of the protein.

Coupling of the phycoerythrin reporter molecule to the detection antibodies in the LAMP-1, saposin C and α-glucosidase assays was achieved using the Molecular Probes (Eugene, Oreg., USA) Protein-Protein Coupling Kit, as per manufacturer's instructions with modifications. There are several published methods known in the art for preparation of phycobiliprotein conjugates with antibodies and other proteins. Generally, the coupling chemistry used to crosslink a phycobiliprotein to another protein includes: (a) treating the antibody or other protein with a succinimidyl ester maleimide derivative at pH 7.5, which converts some lysine residues of the antibody to thiol-reactive maleimides; (b) preparing a thiolated phycobiliprotein by reducing the appropriate SPDP-modified phycobiliprotein with dithiothreitol ("DTT") or with tris-(2-carboxyethyl)phosphine ("TCEP"); (c) mixing the above two dialyzed protein conjugates to yield a stable thio-ether crosslink; and (d) chromatographically separating the phycobiliprotein conjugates from the unreacted proteins.

Figure 12:
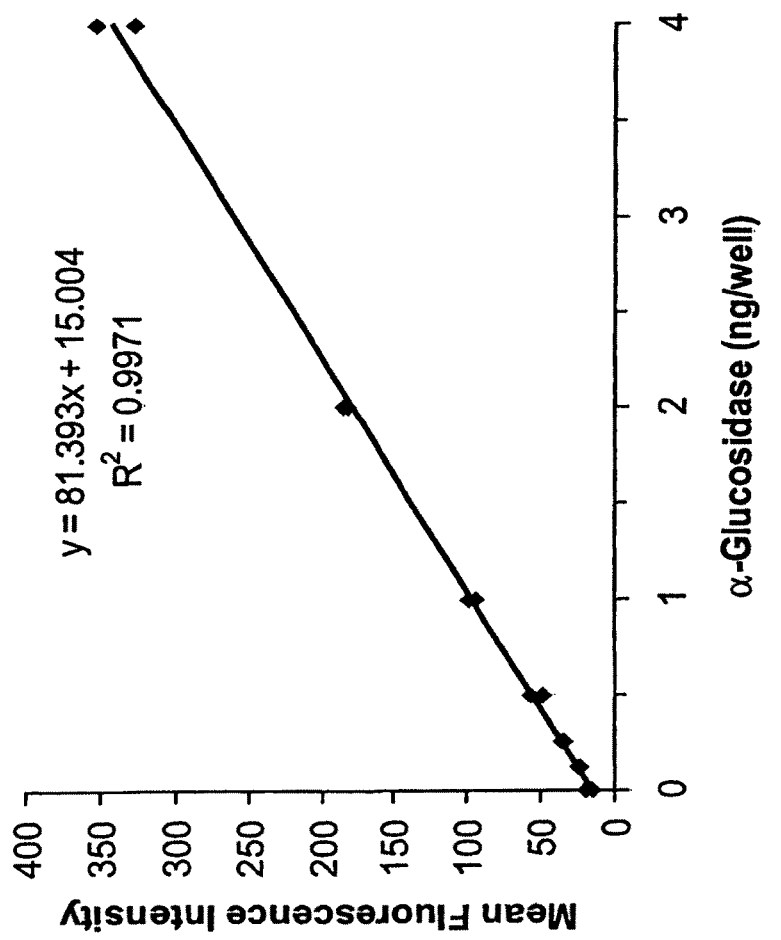
FIG. 12 shows a calibration curve for α-glucosidase in a microsphere based assay.
Figure 13:
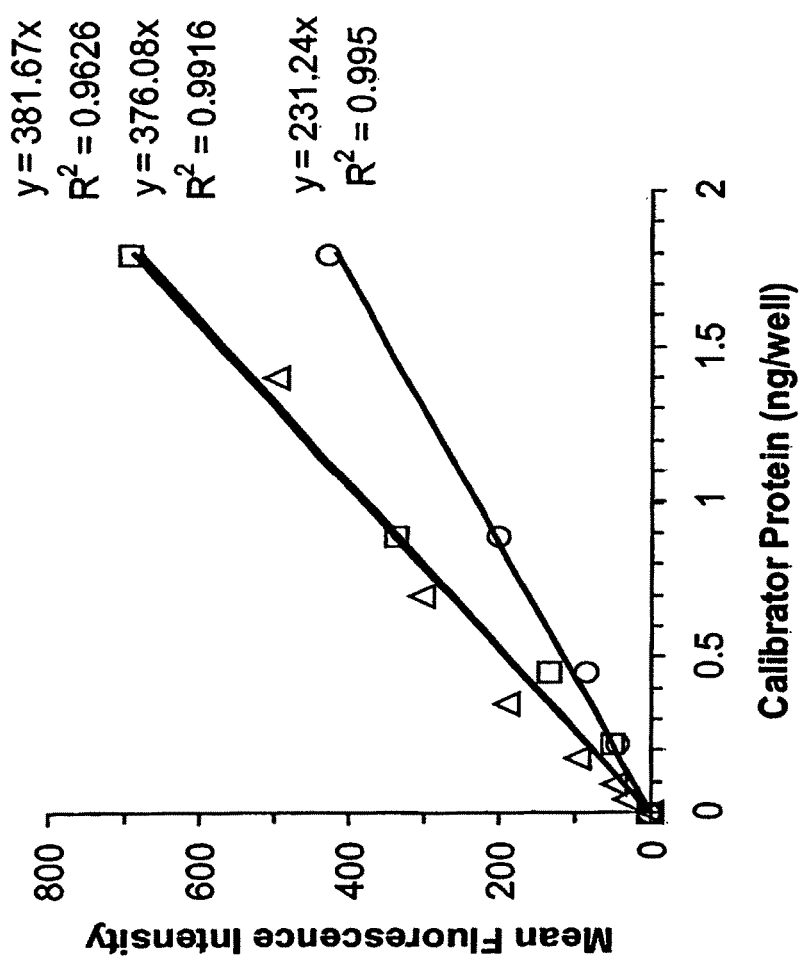
FIG. 13 shows multiplexed calibration curves in a microsphere based assay.

A calibration curve was generated using liquid calibrator proteins in a microsphere based assay using calibrator protein capture antibodies and bead sets #17, #19 and #21 respectively (BioRad, Hercules, Calif., USA). FIG. 12 shows a calibration curve for a single assay for α-glucosidase. The detection capability for the amount of calibrator protein present in each well reaction was linear in the range of 0 to 4 ng/well of the assay. The MFI was the average of the total fluorescence detected for the beads in the defined bead region. Calibration curves were also established, using liquid calibrators, for LAMP-1 (open square), saposin C (open circle), and α-glucosidase (open triangle), as shown in FIG. 13. Increased MFI for the α-glucosidase protein, when compared to FIG. 12, is the result of improvements in the capture antibody labeling of the microspheres and the phycoerythrin reporter labeled antibodies.

Figure 14:
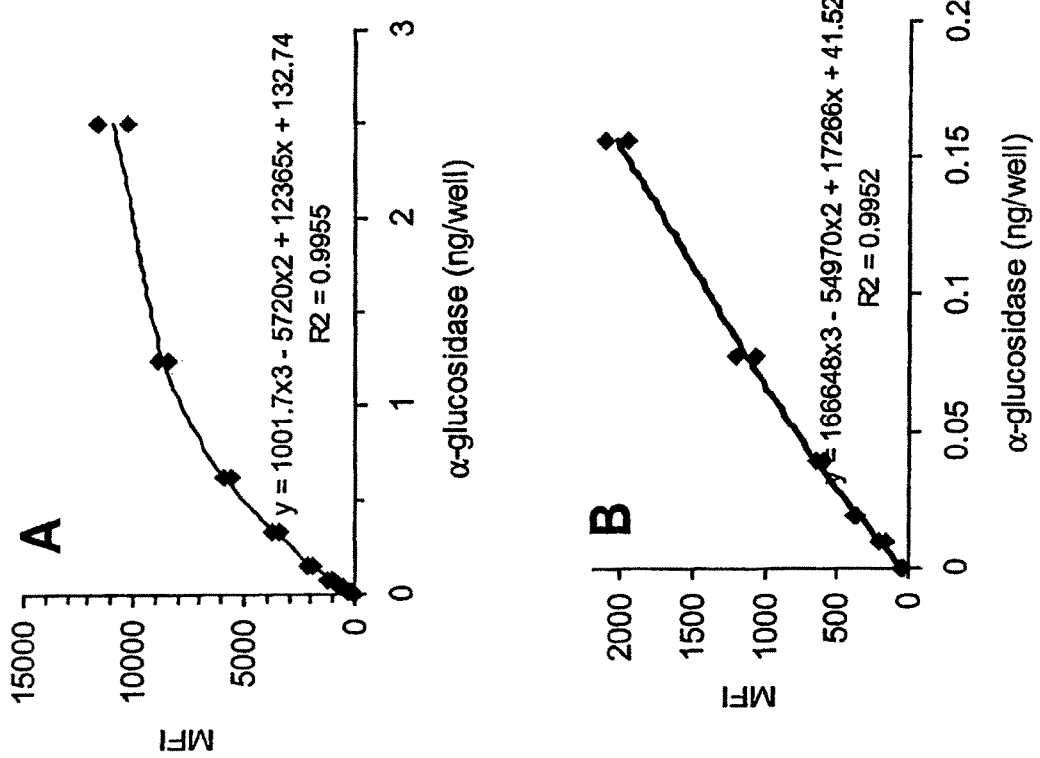
FIG. 14A and FIG. 14B show calibration curves of α-glucosidase using bead technology and measured using BioPlex™ Protein Array system (Bio-Rad)

FIG. 13 also indicates that the detection capability for a multiplex assay of three calibrators was linear from 0 to 2 ng/well of the assay. The sensitivity of the microsphere assay system was also demonstrated with the target capture sheep polyclonal antibody for α-glucosidase and bead set (#19) using a biotinylated reporter antibody with streptavidin-phycoerythrin conjugate (Molecular Probes #S-866). As shown in FIG. 14, α-glucosidase was detectable down to a level of 10 pg/well using this assay. FIG. 14A shows the calibration curve in the range 0-2.5 ng/well, and FIG. 14B shows the same calibration curve expanded in the range 0-0.156 ng/well.

Example 3

Figure 15:
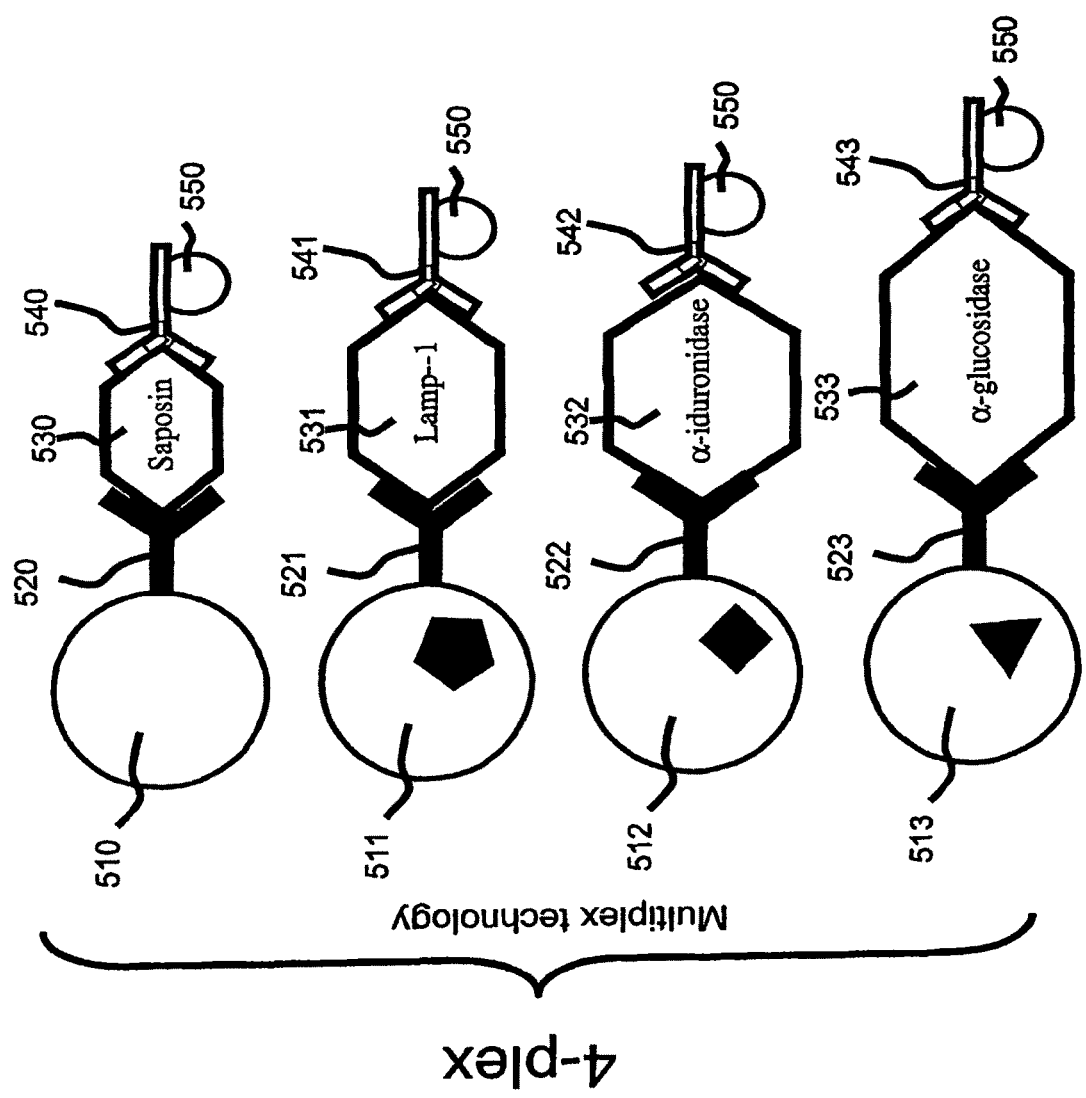
FIG. 15 shows the multiplex technology having at least a 4-plex for LSD's.

Four-Plex Assay for the Determination of LAMP-1, α-Iduronidase, α-Glucosidase and Saposin C A high sensitivity, four-plex assay for target antigens LAMP-1, α-iduronidase, α-glucosidase, and saposin C was developed using the microsphere technology based upon Luminex LABMAP™ technology. As a general illustration, FIG. 15 shows a drawing of a microsphere collection of capture sandwich immunoassays for the 4-plex having: 4 spectrally distinct polystyrene microsphere (510-513); 4 target LSD capture antibody (520-523) bound to the microsphere; 4 unique LSD target proteins or target antigens and representing saposin, LAMP-1; α-iduronidase and α-gulucosidase (530-533) bound to the corresponding target LSD capture antibody; 4 unique detection LSD antibody (540-543); and a detection molecule (550).

Specific Target Capture Microspheres and Target Reporter Antibodies

Specific target capture microspheres and target reporter antibodies were produced using antibodies directed against four specific target proteins (e.g. LAMP-1, α-iduronidase, α-glucosidase, and saposin C), as described above. The sheep anti-α-iduronidase☐ and anti-α-glucosidase polyclonal antibodies were initially purified by ammonium sulphate precipitation. The ammonium sulphate precipitation purified antibodies were further purified using a protein G affinity purification (Amersham Pharmacia 5 ml #17-0404-01). The protein G affinity purified antibodies were finally purified using an Hi trap NHS-activated HP column (Amersham Pharmacia 5 ml #17-0717-01) coupled with either a α-iduronidase or α-glucosidase protein. The antibodies for anti-LAMP-1, anti-α-iduronidase, anti-α-glucosidase, and anti-saposin C were purified from hybridoma supernatant using protein G affinity purification according to manufacturer's specifications (Amersham Pharmacia 5 ml #17-0404-01).

Specific target capture microspheres and target reporter antibodies were produced using antibodies directed against four specific target proteins (e.g. LAMP-1, α-iduronidase, α-glucosidase, and saposin C). Specific target capture microspheres and target reporter antibodies were produced using antibodies directed against four specific target proteins (e.g. LAMP-1, α-iduronidase, α-glucosidase, and saposin C). The capture antibodies were coupled to microsphere beads by a 2-step carbodiimide reaction according to manufacturers instructions (Bio-Rad, Amine coupling kit 171-406001). For example, sheep anti-α-iduronidase ☐and☐, anti-α-glucosidase polyclonal antibodies and anti-saposin C monoclonal antibody (7B2) were coupled to dyed polystyrene beads using the antibody protein amino group via carbodiimide chemistry according to manufacturer's instructions at a concentration of 9 μg of IgG to $1.4 \times 10^6$ beads.

One with ordinary skill in the art is aware of the several published methods known for efficiently biotinylating antibodies and other proteins. For example, the purified anti-LAMP-1, anti-α-iduronidase (Id1A), anti-α-glucosidase (43D1), and anti-saposin C (S13C1) monoclonal antibodies were biotinylated using manufacturer's instructions for a FluoReporter® Biotin-XX Protein labeling kit F-2610 purchased from Molecular Probes (Eugene, Oreg.). Generally, the FluoReporter® Biotin-XX Protein Labeling Kit contains a biotin-XX succinimidyl ester, which reacts with primary amines of proteins or other biomolecules to form stable biotin conjugates. The long spacer between the biotin and the reactive group in biotin-XX succinimidyl ester enhances the ability of the conjugated biotin to interact with the relatively deep biotin-binding sites of avidin and streptavidin. The biotinylated protein was purified from the excess biotin using a gel filtration column. The degree of biotinylation was determined using an avidin-HABA complex and a control biotinylated goat IgG.

Development of Four-Plex Assays.

Figure 16:
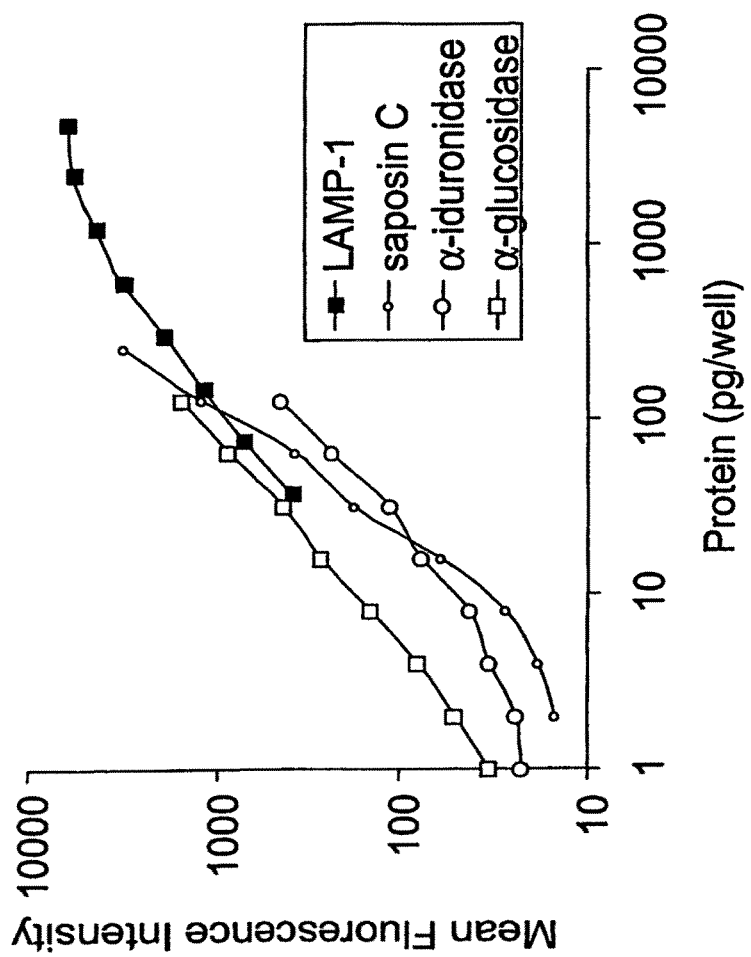
FIG. 16 shows calibration curves for a 4-plex immune quantification of lysosomal proteins.

LSD target antigen capture microspheres were diluted in PBS containing 1% BSA (assay buffer). The diluted LSD target antigen capture microspheres were then added to stock beads in a 96 well filtration plate (Millipore #MABVS1210), wherein the diluted LSD target antigen capture microspheres and stock beads had a total volume of 1 μl per well. Each microwell containing the beads was then washed 3 times with PBS containing 0.05% Tween 20 (wash buffer) under vacuum using a manifold (Millipore #MAVM096OR). Standard solutions containing LAMP-1, α-iduronidase, α-glucosidase, and saposin C protein (50 μl) were added in serial 2-fold dilutions in assay buffer, as indicated. Standards were generated by using the recombinant form of each specific target protein. Biotinylated antibodies (50 μl) were added to each well, wherein the final concentration of each antibody was 16 ng/well in assay buffer. The plate was covered and incubated for 2 hours at room temperature with shaking. The wells were washed, incubated with Streptavidin R-phycoerythrin conjugate (Molecular Probes #S-866) (50 ng/well) in assay buffer for 10 minutes at room temperature with shaking. After a final wash, 125 μl of assay buffer was added per well and the plate shaken for 5 minutes at room temperature. Fluorescence was measured using the Bio-Plex™ Protein Array system in combination with the Bio-Plex™ software version 2.0 (Bio-Rad, Hercules, Calif.). FIG. 16 shows the resulting calibration curves for LAMP-1 (solid square), α-iduronidase (open circle), α-glucosidase (open square), and saposin C (open triangle) of the four-plex assay.

Samples. Plasma and blood samples were collected from infants, children and adults. Although plasma samples and dried blood spots were used as example samples, other suitable sample types are also embodied for this invention (e.g. amniotic fluid, cellular extract, urine, etc.) The plasma and blood spot samples used to demonstrate the four-plex were obtained from the National Referral Laboratory and Neonatal Screening Laboratory Women's and Children's Hospital (Adelaide, Australia) and research laboratories at the Lysosomal Disease Research Unit (Adelaide, Australia). Blood collection and blood spotting techniques are well established, and known by one with ordinary skill in the art.

The bead assays were performed in 96 well filtration plates (Millipore MAV BVS12) and protected from light. Although 96 well filtration plates were utilized, one with ordinary skill in the art understand that other types of sample holders can be used without diverting the scope and spirit of the invention. Plasma samples were diluted in PBS containing 1% BSA (Sigma A-9647) pH 7.2 (assay buffer) at a final concentration of 3 μl/well. Samples derived from 3 mm dried blood spots were pre-eluted overnight at 4° C. in 100 μl of assay buffer in 96 well low protein binding plates (Greiner 655101), wherein 50 μl of each eluted sample was then transferred to a filtration plate. Sample assays and standard assays were performed in duplicate with the exception of the newborn sample blood spots, wherein only a single sample for each newborn was measured.

Following sample preparation, the capture antibody beads were prepared for the multiplex assay. Each individual multiplex assay contained a mixture of capture antibody beads for each of the LAMP-1, α-iduronidase, α-glucosidase, and saposin C capture antibody beads describe above. About 5,000 capture antibodies beads were placed in each sample well of a pre-wetted filtration plate. The mixtures of capture antibody beads were washed 3 times under vacuum in the filtration plate using a wash buffer (PBS, 0.05% Tween 20, pH 7.2), forming a washed/capture bead mixture. Diluted mixed standards or samples prepared as described above were added to the microtiter wells containing the washed/capture bead mixture forming an antigen/bead-set mixture. A mixture of the four biotinylated reporter antibodies (i.e. LAMP-1, α-iduronidase, α-glucosidase, and saposin C) was added to the antigen/bead-set mixture completing assay components.

The plates were sealed and incubated for about 1 hour at room temperature with shaking, then placed at 4° C. overnight under static conditions. The plates were then incubated at room temperature with shaking for about 1 hour. It will be apparent to one skilled in the art of antibody hybridization that incubation conditions can be modified without altering the scope and spirit of the invention. Following incubation, the plates were washed 3 times with wash buffer (PBS, 0.05% Tween 20, pH 7.2) under vacuum. Streptavidin conjugated to phycoerythrin (Molecular Probes S-866) was added to the wells and the plates were incubated at room temperature for 10 minutes. The plates were placed in a Bio-Plex suspension array system (Bio-Rad) and data was collected using Bio-Plex™ Manager software version 3.0 software and counting 100 beads/region. Analysis of the data was determined using a Mann-Whitney U tests (MWU) and box plots using the SPSS statistical package Version 10.0 (SPSS Inc. Chicago, Ill., USA). Percentile cut offs were generated using a standard computer spreadsheet.

Plasma Samples.

The concentrations of LAMP-1, α-iduronidase, α-glucosidase, and saposin C in plasma samples, as determined by the four-plex assay are shown in FIG. 17 and FIG. 18. Briefly, FIG. 17 shows multiplex analysis of control and MPS I plasma, wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box. FIG. 18 shows box plots of plasma concentrations of LAMP-1 (A), saposin C (B), α-glucosidase (C) and α-iduronidase (D) from a control group and 6 different LSD. The center line within the box represents the median. The top of the box is the $75^{th}$ and the bottom of the box is the $25^{th}$ percentile. Error bars represent the largest and smallest values that are not outliers. Outliers represented by open circles and are considered values that are more than 1.5 box lengths from the $75^{th}$ and $25^{th}$ percentile. The extremes are represented by stars having values more than 3 box-lengths from the $75^{th}$ and $25_{th}$ percentile.

Plasma LAMP-1 concentrations (FIG. 18 A) were significantly elevated above controls for the LSD samples measured (MWU Test p<0.05). However saposin (FIG. 18 B) was only elevated in the Gaucher plasma (MWU Test p<0.05). Plasma α-iduronidase levels (FIG. 18 D) were significantly decreased in lysosomal diseases tested with respect to controls (MWU Test p<0.05), except for MPS IIIA. MPS I plasma is normally expected to have negligible if not zero α-iduronidase levels, however, one of the MPS I plasmas has an exceptionally high level of α-iduronidase, which, although not wanting to be bound by theory, probably result from mistargeting of the protein into circulation. From a screening point of view this patients plasma would be flagged for further investigation. Pompe plasma was the only disease group with significantly lower (MWU Test p<0.05) α-glucosidase levels (FIG. 18 C) when compared to control samples.

Although not wanting to be bound by theory, the pattern of LAMP-1 elevation in the 3 disorders as compared to controls observed in the plasma samples was not as apparent in a direct comparison of the target proteins in the sample blood spots (FIG. 19 A) (e.g. none of the disorders had elevated LAMP-1). Similarly no disorder was elevated for saposin C (FIG. 19 B). Although not wanting to be bound by theory, there is an extremely broad range of these four markers in newborns when compared to a tighter range of the same 4 markers in blood spots from older control individuals (i.e. age range 6 months to 47 years). The broad range of absolute levels of the marker protein in infants hinders a defined standard of "elevated" levels of Lamp-1 and saposin C in newborns. Additionally, there was no detectable α-iduronidase and negligible α-glucosidase protein for MPS I and Pompe disease respectively (FIG. 19 C and FIG. 19 D) as compared to the control group in blood spots (MWU Test p<0.001). Some of the newborn control α-iduronidase levels appear to overlap with the zero levels found in MPS I samples but the lowest level for α-iduronidase in newborns was 0.243 ug/L. In contrast to absolute marker measurements, the multiplex allows each protein to be compared using ratios. For example, there was one four month old Pompe patient who had α-glucosidase blood spots levels in the lower range of the control group (FIG. 19 C), this patient would have been missed in a typical screening program if the determined cut-offs used only absolute protein levels. However, using the ratios with the multiplex data, α-glucosidase can be compared against either saposin C (e.g. ratio of 0.271) or LAMP-1 (e.g. ratio of 0.019), whereby flagging this patient as an affected in the $2^{nd}$ percentile. Similar ratio values for the older control range were about 0.339 and about 0.021 for α-glucosidase/saposin C and α-glucosidase/LAMP-1 respectively.

The multiplex data generated for Pompe patients was used to produce a ratio of α-glucosidase to Lamp-1, and this ratio could distinguish 3/3 Pompe plasma samples and 9/9 Pompe blood spot samples from the corresponding plasma and blood spot samples from non-LSD patients. Similarly, the MPS I multiplex ratio data for α-iduronidase to LAMP-1 was below the $2^{nd}$ percentile cut-off for 16/17 plasmas and 4/4 blood spots. As mentioned previously the one rogue MPS I plasma that does not fit the pattern, but still have been flagged as suspicious due to the very high α-iduronidase levels.

Although not wanting to be bound by theory, the specific example of a 4-plex assay supports the invention that a multiplex assay combined with protein profiling of two or more lysosomal proteins improves the detection of MPS I and Pompe affected individuals in both plasma and blood spots. Determination of protein profiles that look at two, three, four or more than four-protein concentrations or corresponding ratios give even more discriminating power to the LSD multiplex assay. One aspect of this invention allows the ratios of LAMP-1 and saposin C to be used as markers to normalize the population for the lysosomal content of the patient sample. For such disorders, these proteins profiles provide additional discriminatory power by showing an increase in concentration relative to the non-disease state. Multiplex technology improves the detection rate for most LSD and has an application in newborn screening programs for these diseases.

As shown in the above examples of the multiplex concept combined with the protein profile/fingerprint concept, there are many ways the profile can be analyzed. Levels of proteins, ratios of proteins and discriminate analysis have been described, but other examples could include the use of neural networks. Therefore, it will be readily apparent to one skilled in the art that various substitutions and modifications may be made in the invention disclosed herein without departing from the scope and spirit of the invention.

Example 4

7-Plex Lysosomal Protein Profile Assay

Protein markers for several LSD disorders are shown in FIG. 20. A 7-plex assay for target antigens LAMP-1, saposin C, α-iduronidase, α-glucosidase, α-galactosidase, β-glucosidase and N-acetylgalactosamine-4-sulphatase was developed using the microsphere technology based upon Luminex LABMAPT™ technology.

Specific Target Capture Microspheres and Target Reporter Antibodies. Specific target capture microspheres and target reporter antibodies were produced using antibodies directed against the seven specific target proteins (e.g. LAMP-1, saposin C, α-iduronidase, α-glucosidase, α-galactosidase, β-glucosidase and N-acetylgalactosamine-4-sulphatase), and the coupling method as outlined above in Example 3. Briefly, the capture antibodies for LAMP-1, saposin C, α-iduronidase, α-glucosidase, α-galactosidase, β-glucosidase and N-acetylgalactosamine-4-sulphatase were coupled to microsphere beads by a 2-step carbodiimide reaction according to manufacturers instructions (Bio-Rad, Amine coupling kit 171-406001). Reporter antibodies were biotinylated according to manufacturers instructions (Molecular Probes, FluoroReporter Biotin-XX protein labelling kit F-2610). The recombinant form of each protein were generated and used as standards. The dried blood spots that were collected from newborns, children and adults and used in this study were samples submitted to the National Referral Laboratory and Neonatal Screening Laboratory Women's and Children's Hospital. Additional samples were collected from within the Lysosomal Disease Research Unit. FIG. 21 shows the antibodies and bead regions used for the 7-plex assay.

Sample Preparation and Method for Multiplexed Assays (7-Plex).

A 3 mm dried blood spots were pre-eluted in 130 μl of filtered (0.2 μm) PBS containing 0.5% BSA (Sigma A-9647), 0.05% γ-globulin (Sigma G-7516) and 0.05% Tween 20, pH7.2, (assay buffer) for 1 hour at room temperature with shaking, followed by 16 h at 4° C. in 96 well, low protein binding plates (Greiner 655101). The blood spots were incubated a further 1 hour at room temperature with shaking and 100 μl of each eluted sample was used for the multiplex assay. Bead assays were performed in 96 well filtration plates (Millipore MAB VNS1250) sealed and protected from light. Samples and standards were performed in duplicate except for the newborn blood spots where only single samples were used.

Antibody coated beads (5,000/well) for each individual assay were mixed and placed into pre-wetted filtration plates and the supernatant removed by vacuum. Diluted pre-mixed standards or samples were added to the beads followed by the 7 pre-mixed biotinylated reporter antibodies. The plates were incubated for 1 hour at room temperature with clinking, then placed at 4° C. overnight. After a further 1 hour incubation at room temperature with shaking, the plates were washed 3 times with filtered (0.2 μm) PBS containing 0.05% Tween 20, pH 7.2 (wash buffer) under vacuum. Streptavidin conjugated to phycoerythrin (Molecular Probes S-866) was diluted in assay buffer (1.5 ug/mL) and added to the wells (100 μl/well), then the plates were incubated at room temperature with shaking for 10 minutes. The plates were then read on the Bio-Plex suspension array system (Bio-Rad) using version 3.0 software and counting 100 beads/region.

Results for Multiplexed Assays (7-Plex).

Control blood spots from 12 adult and 28 newborn control individuals were assayed for the 7 lysosomal proteins; LAMP-1, saposin C, α-iduronidase, α-glucosidase, α-galactosidase, β-glucosidase and N-acetylgalactosamine-4-sulphatase. FIG. 22 shows the calibration curves for each of the protein assays. FIG. 23 shows the individual and average adult control protein values in the 7 plex assay obtained for each sample with the standard deviation, minimum and maximum of each group. FIG. 24 shows the individual and average newborn protein values in the 7 plex assay for each sample with the standard deviation, minimum and maximum of each group. Standard deviation, minimum and maximum are also presented as multiples of the mean (MOM). Comparison of the standard deviation, minimum and maximum MOM values for the adult and newborn groups show that the newborn group has a wider range than the adult group.

FIG. 25 shows the Pearson correlation coefficient between each pair of target protein analytes. With the exception of α-iduronidase, the target antigens showed a significant correlation to the other target antigens.

Dried blood spot samples from 16 LSD affected individuals representing 5 different disorders were also analysed with the 7-plex protein profile. The results of these analyses are shown in FIG. 26 (compared to the adult control group) and FIG. 27 (compared to the newborn control group). The LSD patients were clearly distinguished from the control groups.

Example 5

Multiplex Method to Screen the Newborn Population for Major LSD's

A general multiplex neonatal screening strategy for LSD is illustrated in FIG. 28. A neonatal screening strategy for LSD's can be customized depending upon the geographic region and LSD prevalence. For example, the following 14-Plex is an example of an assay suitable for use in North America and Europe. Twelve specific LSDs were chosen because of their relatively high prevalence in North America and Europe, together with the availability of effective therapies that would benefit from early diagnosis. A multiplex assay for the following 14 target proteins can test for the associated LSD that is shown in parentheses: LAMP-1 (generic LSD), saposin C (generic LSD), α-glucosidase (Pompe), α-galactosidase A (Fabry), glucocerebrosidase or β-glucosidase (Gaucher), α-iduronidase (MPS I), iduronate-2-sulphatase (MPS II), heparan-N-sulphatase (MPS IIIA), α-N-acetylglucosaminidsse (MPS MB), galactose-6-sulphatase (MPS IVA), β-galactosidase or galactocerebrosidsse (Krabbe), galactose-3-sulphatase (MLD), sphingomyelinase (Niemann-Pick A/B) and N-acetylgalactosamine-4-sulphatase (MPS VI).

The protein profiling multiplex technology enables combinations of LSD target antigens to be modified as LSD treatment methods improve, as new LSD are identified, or screening needs change in different geographic areas. Antibodies to each of the 14 LSD target antigens are needed for this 14-plex assay.

The present invention improves the accuracy and detection of each of the LSD's in a single multiplex assay. The target antigens LAMP-1 and saposin C are used as markers to normalize the population for the lysosomal content of the patient sample. For some disorders, these proteins may provide additional discriminatory power by showing an increase in concentration relative to the non-disease state. By calculating the ratio of these proteins to the individual proteins deficient in each LSD, greater discriminatory power can be attained. This concept can be extended beyond the calculation of ratios of individual proteins to the determination of protein profiles that encompasses many different target antigen protein concentrations for a given sample. The use of discriminate analysis or other statistical methods can provide improved discrimination between control and affected populations.

Protein profiling will improve the sensitivity and specificity of determining an LSD, wherein false negatives can be optimized to a sensitivity of 0-20% for most LSD's and false positives can be predicted between 0.1% and 0.01%. Additionally, confirmation assays can be performed on all positive assays prior to recalling the patient. Confirmation testing for LSD type following Multiplex protein profiling can be completed by methods such as specific enzyme analysis, substrate storage analysis, or genotyping. Enzyme analysis comprises immune capture assay for specific lysosomal enzymes that are performed on a second blood spot. The substrate storage analysis comprises oligosaccharide and glycolipid analysis performed on second and third blood spots. Genotyping from dried blood spots comprises screening for common mutations where appropriate on a further blood spots.

It is understood that proteins characteristic of other LSD types can be replaced, or added to the 14 target antigen lysosomal proteins listed above and that such modifications may depend on the frequency of individual LSD's for particular geographic regions. For example, the relative prevalence of individual LSD's is different in North America, Japan and China. It is also understood that other biomolecules can represent the specific LSD target antigens or target molecules, such as antibodies, DNA sequences or RNA sequences or protein activities may be used or measured for the purposes multiplexing and profiling of target biomolecules this invention.

Example 6

Developing a Multiplex Profiles for a LSD

In one embodiment of the invention a series of at least two lysosomal proteins (e.g. α-glucosidase, β-glucosidase, α-galactosidase, α-iduronidase, iduronate-2-sulphatase and N-acetylgalactosamine-4-sulphatase, etc.) are multiplexed. Samples from a control population (n≥100) are analyzed with the multiplexed assay to determine the normal range for each of the analytes. Each analyte is normalized to general lysosomal markers (e.g. LAMP-1 and saposin C) in addition to the other specific markers to produce a series of ratios, or a fingerprint table. These ratios are then used to provide a profile of the control population. Samples from, a target population (Pompe, Gaucher, and other LSD affected individuals) (n≥20) are analyzed and the results normalized as described in previous examples. The specific ratios that best differentiate the control and target populations are then utilized develop a specific profile/fingerprint of the LSD disease state.

Example 7

Multiplex Profiles for Specific a LSD

In one embodiment of the invention a series of at least two lysosomal proteins (e.g. α-glucosidase, β-glucosidase, α-galactosidase, α-iduronidase, iduronate-2-sulphatase and N-acetylgalactosamine-4-sulphatase, etc.) are multiplexed and utilized as a specific disease diagnostic (e.g. Pompe, Gaudier, Fabry, MPS, Niemann-Pick, Krabbe, etc.). Samples from a control population of patients are analyzed with the specific LSD multiplexed assay to determine the normal range for each of the analytes in the control population. Each analyte is normalized to the general lysosomal markers (e.g. LAMP-1 and saposin C) in addition to the other specific markers to produce a series of ratios. These ratios are then used to provide a profile of the control population. Samples from a target population of patients (e.g. Pompe, Gaudier, Fabry, MPS, Niemann-Pick, Krabbe, etc.) are also analyzed to determine the diseased state reference range of each analyte in a target disease population. The level of each analyte in the target population is identified as being elevated, decreased or unchanged, relative to the control population. This provides a protein profile or fingerprint for the target disease state. Target populations representing each LSD of interest can be analyzed by this method and specific profiles/fingerprints can be obtained. Samples from patients with an unknown TSD clinical status are then analyzed and the resulting patterns compared with the available target protein profiles to identify the specific LSD disease.

Example 8

Multiplex Profiles for LSD Disease Progression and Therapy Monitoring

At least two lysosomal proteins (e.g. LAMP-1, saposin C, α-glucosidase, β-glucosidase, α-galactosidase, α-iduronidase, iduronate-2-sulphatase and N-acetylgalactosamine-4-sulphatase, etc) are multiplexed. Samples from a control population are analyzed with the multiplexed assay to determine the normal range for each of the analytes. Samples from a population of individuals affected with a specific LSD (e.g. Pompe, Gaucher, Fabry, MPS, Niemann-Pick, Krabbe, etc.) in are also analyzed to determine the reference range of each analyte in the LSD affected population. The two sets of data are used as a training data set to perform discriminate analysis. This discriminate analysis will allow the identification of the LSD disease affected individuals from the control population and classification for each LSD patient that is correlated to the disease severity (phenotype), or provide a prediction of phenotype (disease progression) in asymptomatic patients. Samples taken from a LSD affected individual at different times during the course of therapy are analysed. The discriminate function is used to determine the degree of normalisation of the protein profile for that individual (i.e how close does it approach the control profile) and thereby monitor the efficacy of therapy.

Example 9

Multiplex Profiles for Pompe

In one embodiment of the invention a series of at least two lysosomal proteins (e.g. α-glucosidase, β-glucosidase, α-galactosidase, α-iduronidase, iduronate-2-sulphatase and N-acetylgalactosamine-4-sulphatase, etc.) are multiplexed and utilized as a specific disease diagnostic for Pompe disease. Samples from a control population (n≥100) of patients are analyzed with the specific LSD multiplexed assay to determine the normal range for each of the analytes in the control population. Each analyte is normalized to the general lysosomal markers (e.g. LAMP-1 and saposin C) in addition to the other specific markers to produce a series of ratios. These ratios are then used to provide a profile of the control population. Samples from a target population of patients Pompe (n≥20) are also analyzed to determine the LSD state reference range of each analyte in Pompe disease population. The level of each analyte in the Pompe population is identified as being elevated, decreased or unchanged, relative to the control population. This provides a protein profile or fingerprint for the Pompe disease state. Target populations representing each level of Pompe severity of interest can be analyzed by this method and specific profiles/fingerprints can be obtained. Samples from patients with an unknown LSD clinical status are then analyzed and the resulting patterns compared with the available target protein profiles to identify the specific Pompe LSD disease. Additionally, the discriminate function can be used determine the degree of normalization of the protein profile for that individual (i.e. how close do the values approach the control profile) and thereby monitor the efficacy of a therapy.

Example 10

Multiplex Newborn Screening

In one embodiment of the invention a series of lysosomal proteins (LAMP-1, saposin C, α-glucosidase, β-glucosidase, α-galactosidase, α-iduronidase, iduronate-2-sulphatase and N-acetylgalactosamine-4-sulphatase) are multiplexed. Samples (e.g., dried blood spots) from newborns in a given population are analyzed for a specific LSD (e.g. none, Pompe, Gaucher, Fabry, MPS, Niemann-Pick, Krabbe, etc.) based on protein profiles/fingerprints of discriminate functions as described in Examples 5-9 above. The newborns are then assigned a probability of being affected by a LSD, wherein further testing may be required for newborns verification.

Example 11

Multiplex and Cancer

At least two lysosomal proteins (e.g. LAMP-1, saposin C, α-glucosidase, β-glucosidase, α-galactosidase, α-iduronidase, iduronate-2-sulphatase and N-acetylgalactosamine-4-sulphatase, etc) or cancer antigens are multiplexed. Samples from a control population are analyzed with the multiplexed assay to determine the normal range for each of the analytes. Samples from a target population (e.g. cancer affected individuals) are also analyzed to determine the reference range of each analyte in this population. The two sets of data are used as a training set to perform discriminate analysis and identify a discriminate function that will enable the separation of the cancer affected individuals from the control population. The discriminate function is then used to identify patients having an unknown protein profile consistent with the particular cancer under investigation. This embodiment thereby provides early identification of the cancer.

Multiplex LSD protein profiling provides solutions to many issues relating to newborn screening assays. For example, multiplex LSD protein profiling provides sensitivity and specificity required to diagnose a specific selection of LSD disorders to be screened, wherein additional lysosomal proteins can be added if needed. Multiplex LSD protein profiling also provides a platform technology to undertake screening for other LSD populations (e.g. Renal/cardiac clinics for Fabry disease; accociation of Fabry disease w/end-stage renal failure, and association of Fabry disease w/idiopathic cardiomyopathy, muscle fatigue/soreness for adult Pompe disease, and altered lysosomal function and protein levels in some types of cancers). Multiplex LSD protein profiling is also flexable to incorporate non-lysosomal protein markers (e.g. thyroid stimulating hormone, immunoreactive trypsin and others.)

This invention comprises lysosomal protein profiling for LSD, which encompasses the use of protein marker ratios using existing LSD target markers that are increased with LSD, and the use additional LSD target markers that are decreased with LSD. Protein profiling also utilizes a ratio of the LSD target markers to improve discrimination. Some LSD markers can be used to correct for lysosome/leukocyte levels. Additionally ratio specific markers (e.g. LAMP-1) can be utilized to correct for different lysosomal content and other ratio markers can be utilized to correct for white cell content (e.g. CD45). Protein profiles incorporate different proteins markers that are measured to improve discrimination. Although Multiplex bead technology has been used as a specific example, other methods of multiple LSD target protein measurements can be utilized to perform protein profiling. Such methods do not deviate from the spirit and scope of the claimed invention.

REFERENCES CITED

The following references, to the extent that they provide exemplary procedural or other details supplementary to those set forth herein, are specifically incorporated herein by reference.

U.S. Patent Documents

U.S. Pat. No. 6,449,562 ("the '562 patent") entitled "Multiplexed Analysis of Clinical Specimens Apparatus and Method," having Chandler et al. listed as inventors was issued on Sep. 10, 2002.
U.S. Pat. No. 6,524,793 ("the '793 patent") entitled "Multiplexed Analysis of Clinical Specimens Apparatus and Method," having Chandler et al. listed as inventors, was issued on Feb. 25, 2003.
U.S. patent application Ser. No. 09/956,857 ("the '857 Application") entitled "Multiple Reporter Read-out for Bioassays" was published on Mar. 20, 2003.
PCT Application AU03/00731 entitled "identification of Oligosaccharides and their Use in the Diagnosis and Evaluation of Mucopolysaccharidoses and Other Related Disorders," having Hopwood et al., listed as inventors, filed on Jun. 13, 2003

Other Publications

Carlsson, S. R., M. Fukuda, Structure of human lysosomal membrane glycoprotein 1, Assignment of disulfide bonds and visualization of its domain arrangement, *J. Biol. Chem.* 264:20526-20531 (1989).
Fransen, J. A., L. A. Ginsel, P. H. Cambier, J. Klumperman, R. P. Oude Elferink, J. M. Tager, immunocytochemical demonstration of the lysosomal enzyme alpha-glucosidase in the brush border of human intestinal epithelial cells, *Eur J Cell Biol* 47:72-80 (1988).
Harlow, E., D. Lane, *Antibodies, A laboratory manual*, Cold Spring Harbor Laboratory (1988).
Hua, C. T. et al., Evaluation of the lysosome-associated membrane protein LAMP-2 as a marker for lysosomal storage disorders, *Clin. Chem.* 44(10): 2094-2102 (1988).
Isbrandt, D., G. Arlt, D. A. Brooks, J. J. Hopwood, K. von Figura, and C. Peters, Mucopolysaccharidosis VI (Maroteaux-Lamy syndrome): Six unique arylsulfatase B gene alleles causing variable disease phenotypes, *Am J Hum Genet.* 54(3): 454-63 (1994).
Meikle et al., Prevalence of lysosomal storage disorders, *JAMA* 281: 249-254 (1999).
Neufeld, E. F. and J. Muenzer, The mucopolysaccharidoses, *The Metabolic & Molecular Basis of Inherited Disease, 7th Edition.*, pp. 2465-2494 (1995).
Umapathysivam, K., J. J. Hopwood, P. J. Meikle, Determination of acid alpha-glucosidase activity in blood spots as a diagnosis for Pompe Disease, *Clin. Chem.* 47(8): 1378-1383 (2001).

Zola, H., D. Brooks, Techniques for the Production and Characterization of Monoclonal Hybridoma Antibodies, *Monoclonal Hybridoma Antibodies: Techniques and Applications* (1982).

The claims defining the invention are as follows:

1. A composition used for diagnosing a lysosomal storage disorder ("LSD") comprising:
   a set of capture antibodies conjugated to microspheres, each microsphere having a different specific capture antibody and having at least a first fluorophore and a second fluorophore wherein the first fluorophore and the second fluorophore are spectrally distinct, wherein the set of capture antibodies comprises antibodies capable of binding to α-iduronidase, α-glucosidase, LAMP-1, and saposin C; and
   wherein each microsphere conjugated to a specific capture antibody has a specific ratio of the first fluorophore to the second fluorophore; and
   wherein each microsphere conjugated to a specific capture antibody is spectrally distinct from a microsphere conjugated to a different capture antibody.

2. The composition of claim 1, further comprising a detection antibody, wherein the detection antibody is capable of binding the target antigen, but is different from the capture antibody; and the detection antibody is conjugated to a detection label.

3. The composition of claim 1, wherein the microsphere has a diameter of about 5 μm.

4. The composition of claim 1, wherein the LSD is selected from the group consisting of Fabry; Mucopolysaccharidosis type I ("MPS I"); Mucopolysaccharidosis type II ("MPS-II"); Mucopolysaccharidosis type III ("MPS-III'); Mucopolysaccharidosis type IV ("MPS-IV"); and Glycogen storage disease II ("Pompe").

5. The composition of claim 1, wherein the LSD is selected from the group consisting of Gaucher disease types I/II/III; Cystinosis; Mucopolysaccharidosis type VI; Mucopolysaccharidosis type IVA; Niemann-Pick disease types A/B; Metachromatic leucodystrophy; Metachromatic leucodystrophy; Mucopolysaccharidosis type IIIA; Mucopolysaccharidosis type IIIB; Mucopolysaccharidosis type IIIC; Mucopolysaccharidosis type IIID; Mucopolysaccharidosis type VII; Mucopolysaccharidosis type IVB; Niemann-Pick disease type C1; Niemann-Pick disease type C2; Cholesterol ester storage disease; Aspartylglucosaminuria; GM1-Gangliosidosis types I/II/III; GM2-Gangliosidosis type I; GM2-Gangliosidosis type II; GM2-Gangliosidosis; Farber Lipogranulomatosis; β-Mannosidosis; Galactosialidosis types I/II; α-Mannosidosis types I/II; β-Mannosidosis; Mucolipidosis type I; Mucolipidosis types II/III; Mucolipidosis type IIIC; Mucolipidosis type IV; Multiple sulphatase deficiency; Neuronal Ceroid Lipofuscinosis, CLN1; Neuronal Ceroid Lipofuscinosis, CLN2; Neuronal Ceroid Lipofuscinosis, CLN3; Neuronal Ceroid Lipofuscinosis, CLN5; Neuronal Ceroid Lipofuscinosis, CLN8; Pycnodysostosis; and Sialic acid storage disease.

* * * * *